United States Patent
Shetty

(10) Patent No.: US 10,660,931 B2
(45) Date of Patent: *May 26, 2020

(54) HERBO-MINERAL FORMULATION FOR THE TREATMENT OF CANCER AND METHOD OF PREPARATION THEREOF

(71) Applicant: Muniyal Ayurvedic Research Centre, Manipal (IN)

(72) Inventor: M Vijayabhanu Shetty, Karnataka (IN)

(73) Assignee: MUNIYAL AYURVEDIC RESEARCH CENTRE, Manipal (IN)

(*) Notice: Subject to any disclaimer, the term of this patent is extended or adjusted under 35 U.S.C. 154(b) by 0 days.

This patent is subject to a terminal disclaimer.

(21) Appl. No.: 15/945,389

(22) Filed: Apr. 4, 2018

(65) Prior Publication Data

US 2018/0289765 A1     Oct. 11, 2018

Related U.S. Application Data

(60) Provisional application No. 62/482,558, filed on Apr. 6, 2017.

(51) Int. Cl.

| | | |
|---|---|---|
| A61K 36/9066 | (2006.01) | |
| A61K 45/06 | (2006.01) | |
| A61K 36/81 | (2006.01) | |
| A61K 36/185 | (2006.01) | |
| A61K 36/88 | (2006.01) | |
| A61K 36/59 | (2006.01) | |
| A61K 36/68 | (2006.01) | |
| A61K 36/53 | (2006.01) | |
| A61K 35/04 | (2006.01) | |
| A61K 35/02 | (2015.01) | |
| A61K 33/00 | (2006.01) | |
| A61K 33/30 | (2006.01) | |
| A61K 35/614 | (2015.01) | |
| A61K 33/26 | (2006.01) | |
| A61K 9/20 | (2006.01) | |
| A61P 35/00 | (2006.01) | |
| A61K 36/67 | (2006.01) | |
| A61K 36/8965 | (2006.01) | |
| A61K 36/47 | (2006.01) | |
| A61K 36/9068 | (2006.01) | |

(52) U.S. Cl.
CPC .......... *A61K 36/9066* (2013.01); *A61K 9/205* (2013.01); *A61K 33/00* (2013.01); *A61K 33/26* (2013.01); *A61K 33/30* (2013.01); *A61K 35/02* (2013.01); *A61K 35/04* (2013.01); *A61K 35/614* (2013.01); *A61K 36/185* (2013.01); *A61K 36/47* (2013.01); *A61K 36/53* (2013.01); *A61K 36/59* (2013.01); *A61K 36/67* (2013.01); *A61K 36/68* (2013.01); *A61K 36/81* (2013.01); *A61K 36/88* (2013.01); *A61K 36/8965* (2013.01); *A61K 36/9068* (2013.01); *A61K 45/06* (2013.01); *A61P 35/00* (2018.01)

(58) Field of Classification Search
CPC . A61P 35/00; A61K 36/8965; A61K 36/9068; A61K 36/9066; A61K 36/258; A61K 9/205; A61K 35/00
See application file for complete search history.

(56) References Cited

U.S. PATENT DOCUMENTS

2002/0136783 A1*   9/2002   Singh .................. A21D 2/36
                                                              424/725

FOREIGN PATENT DOCUMENTS

IN        200701734 I2      3/2008

OTHER PUBLICATIONS

Chaudhary, IN 200500769 I2, Derwent English abstract from EAST, Mar. 24, 2006 (Year: 2006).*
Zhang et al., "Two new vinblastine-type N-oxide alkaloids from Catharanthus roseus," Nat Prod Res, Oct. 2013, pp. 1911-1916, vol. 27, abstract.

* cited by examiner

*Primary Examiner* — Mark V Stevens
(74) *Attorney, Agent, or Firm* — Pilloff Passino & Cosenza LLP; Sean A. Passino; Rachel K. Pilloff

(57) ABSTRACT

Herbo-mineral formulation for the treatment of cancer and method of preparation are disclosed herein. The disclosed formulation includes a combination of herb and mineral components that facilitate in controlling abnormal cell proliferation. The formulation can thus be used in treatment of cancer and related mobidities.

15 Claims, 14 Drawing Sheets

# HERBO-MINERAL FORMULATION FOR THE TREATMENT OF CANCER AND METHOD OF PREPARATION THEREOF

CROSS REFERENCE TO RELATED APPLICATION

This application is based on and derives the benefit of U.S. Provisional Application 62/482,558 filed on Apr. 6, 2017, the contents of which are incorporated herein by reference.

TECHNICAL FIELD

The embodiments disclosed in this specification relates to herbo-mineral formulation effective in treatment of cancer and associated complications. It also relates to the process for preparation of such formulation.

BACKGROUND

Cell proliferation is a highly regulated activity. Most cells are in a non-proliferative state unless they are stimulated. The loss of proliferative control leads to undesired abnormal cell proliferation and accumulation. Such accumulation of abnormal cells, commonly referred to as tumor, is a main characteristic of Cancer. Cancer can be of various types such as sarcoma, lymphoma, leukemia, melanoma, etc, depending on the type of cell that may be affected.

Cancer is one of the most dreaded diseases. It is considered to be a leading cause of death worldwide. For years, pharmaceutical industries and research institutes have been making best efforts in finding an effective treatment for cancer.

Modern medicine offers various methods for treating cancer including chemotherapy, radiation therapy, hormone therapy, targeted therapy etc. The type of treatment opted depends on location and stage of cancer. Although, evolutionary changes have occurred over the years in finding a treatment for cancer, these methods have been observed to have drawbacks. These commonly used treatment methods tend to affect healthy tissue, in addition to cancer tissues, thereby resulting in side effects such as Alopecia, Lymphedema, Pain, Bleeding, Bruising, Edema, Skin and Nail changes, Fertility problems, etc. These side effects in turn have adverse effects on patients, at a physical, mental, emotional and social level.

Alternatively, ayurvedic medicine has also been used to treat cancer. With the knowledge of the anti-tumor properties of herbs such as *Silybum marianum, Aloe barbadensis, Curcuma longa, Zingiber officinale, Hydrastis canadensis, Annona muricata*, etc, numerous herbal formulations including such herbs have been developed. However, the effectiveness of such formulations is arguable and inconsistent. There exists a need for an effective method of treating abnormal cell proliferation leading to cancer.

OBJECT OF THE DISCLOSED EMBODIMENTS

The principal object of the embodiments disclosed herein is to provide a composition and method of treating cancer.

Another object of the embodiments disclosed herein is to provide a composition and method of inducing cytotoxicity and growth inhibitory effect in cancerous cells.

Further, it is also an object of the embodiments disclosed herein to provide a composition and method of improving general health conditions of an individual prone to or suffering from Cancer.

Yet another object of the embodiments disclosed herein is to provide a herbo-mineral formulation and a method for its preparation.

These and other objects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

The embodiments disclosed herein are illustrated in the accompanying drawings, throughout which like reference letters indicate corresponding parts in the various figures. The embodiments herein will be better understood from the following description with reference to the drawings, in which:

FIG. 1(*b*) depicts a flowchart for the preparation of Abhraka Bhasma;

FIG. 1(*c*) depicts a flowchart for the preparation of Loha Bhasma;

FIG. 1(*d*) depicts a flowchart for the preparation of Trivanga Bhasma;

FIG. 1(*e*) depicts a flowchart for the preparation of Pravala Bhasma;

FIG. 3(*b*) is an illustration of the results of the TLC analysis under UV light (7 cm), at UV 366;

FIG. 3(*c*) is an illustration of the results of the TLC analysis under white light;

FIG. 3(*d*) is an illustration of the results of the TLC analysis under UV light (12 cm);

FIG. 3(*e*) is an illustration of the results of the TLC analysis under UV light (12 cm), at UV 254;

FIG. 3(*f*) is an illustration of the results of the TLC analysis under UV light (12 cm), at UV 366.

FIG. 6(*b*) is a graph depicting the cytotoxicity of test drug on HeLa cell line; and;

FIG. 6(*c*) is a graph depicting the cytotoxicity of test drug on SKOV3 cell line, according to embodiments as disclosed herein.

DETAILED DESCRIPTION

Figure 1A:
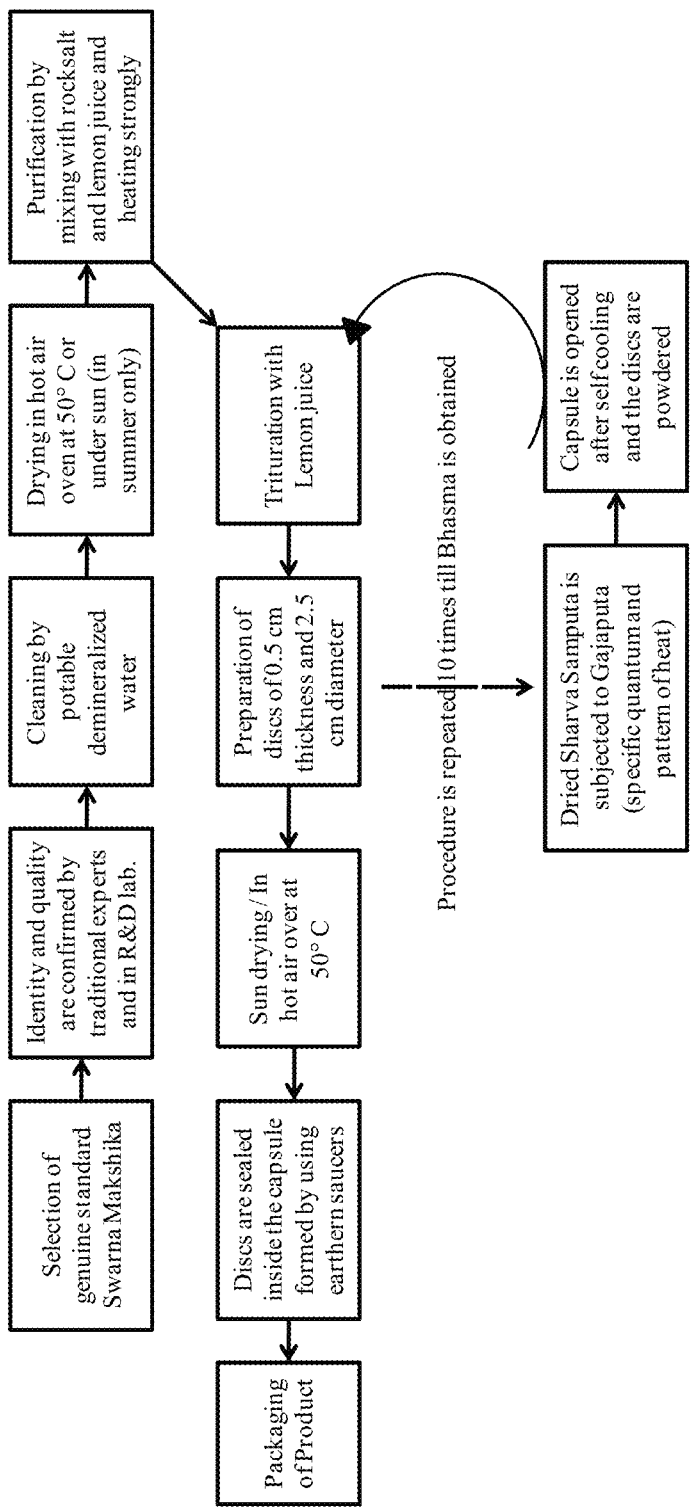
FIG. 1(*a*) depicts a flowchart for the preparation of Swarna Makshika Bhasma.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein achieve a herbo-mineral formulation of therapeutic value, and a process for the preparation of the formulation. The herbo-mineral formulation disclosed in the various embodiments herein is having anti-cancer properties and is useful in the treatment of cancer. The disclosed formulation in various embodiments herein is instrumental in inducing cancer cell cytotoxicity and apoptosis. It has further been observed, in various embodiments, to have antiproliferative and growth inhibitory effect on cancerous cells.

The formulation disclosed in the various embodiments herein may be used in treating any type of cancer. It may be used to improve the general health of individuals having a condition involving abnormal, unregulated cell proliferation such as carcinoma of oesophagus, carcinoma of lung, bronchogenic carcinoma, adenocarcinoma of endometrium, adenocarcinoma of rectum, Non-Hodgkin's lymphoma, chronic myeloid leukemia, borderline mucinous tumor, adenocarcinoma of colon, fibro sarcoma, ovarian carcinoma, carcinoma of pancreas etc. Accordingly, the embodiments herein achieve a method for the treating.

Formulation

The disclosed embodiments herein provide a herbo-mineral formulation having a combination of selected herbs and minerals. In an embodiment, the herbo-mineral formulation includes a herb component and a mineral component. In another embodiment, the herbo-mineral formulation includes a herb component, a mineral component and a suitable excipient.

Herb Component

In an embodiment, the herb component includes the herbs *Withania somnifera*, *Sida cordifolia*, *Asparagus racemosus*, *Tinospora cordifolia*, *Moringa oleifera*, *Picrorhiza kurroa*, *Ocimum sanctum* and *Curcuma longa*, or their extracts, or the active ingredients extracted from these herbs. In another embodiment, the herb component further includes at least one of the herbs selected from *Terminalia chebula*, *Terminalia bellerica*, *Emblica officinalis*, *Piper longum*, *Piper nigrum* and *Zingiber officinalis* or their extracts, or the active ingredients extracted from these herbs.

In an embodiment, the herb component may include specific parts of the herb (also referred as herb component) such as roots, fruits, stem, leaves, rhizome, etc. In an embodiment, the herb component may include roots of *Withania somnifera*, *Sida cordifolia*, *Asparagus racemosus* and *Picrorhiza kurroa*; fruit of *Terminalia chebula*, *Terminalia bellerica*, *Emblica officinalis*, *Piper longum* and *Piper nigrum*; stem of *Tinospora cordifolia*; rhizome of *Zingiber officinalis* and *Curcuma longa*; stem bark of *Moringa oleifera* and leaves of *Ocimum sanctum* or their extract. However, it is also within the scope of the claims provided herein for the herbo-mineral formulation to include other herb components such as leaf, flowers, etc. without otherwise deterring intended function of the herbo-mineral formulation.

The herb component may be included in the formulation in any form that is generally known in the field. For example, the herb component may be dried, powdered, processed to form concentrates, extracts, etc. In one preferred embodiment, the herb components are dried and powdered which is further incorporated into the formulation.

In an embodiment, the herb component includes *Withania somnifera* in the range of 6 to 10 wt %, *Sida cordifolia* in the range of 6 to 10 wt %, *Asparagus racemosus* in the range of 4 to 8 wt %, *Tinospora cordifolia* in the range of 4 to 8 wt %, *Moringa oleifera* in the range of 4 to 8 wt %, *Picrorhiza kurroa* in the range of 4 to 8 wt %, *Ocimum sanctum* in the range of 4 to 8 wt %, and *Curcuma longa* in the range of 5 to 9 wt %. Further, in another embodiment, the herb component includes at least one of *Terminalia chebula*, *Terminalia bellerica*, *Emblica officinalis*, *Piper longum*, *Piper nigrum* and *Zingiber officinalis* an amount in the range of 2 to 6 wt %.

Mineral Component

In an embodiment, the mineral component includes Bhasmas or calcined preparations such as Swarna Makshika bhasma, Abhraka bhasma, Loha bhasma, Trivanga bhasma, and Pravala bhasma. Alternatively, the mineral component may also be selected from a group consisting of at least one of mica, tin, lead, zinc, coral, iron and copper pyrite.

In the disclosed embodiments, the bhasmas along with the herb component form bioavailable herbo-mineral complexes which are useful in treating cancer. In another embodiment, the mineral component includes Shilajit. However, it is also within the scope of claims provided herewith for the herbo-mineral formulation to include, as a substitute or additionally, other similar calcined preparations or minerals without otherwise deterring from the intended function of the herbo-mineral formulation.

In an embodiment, the mineral component includes shilajit in the range of 4 to 8 wt %. In another embodiment, the mineral component includes Abhraka Bhasma in the range of 2 to 4 wt %, Trivanga Bhasma in the range of 0 to 2 wt %, Pravala Bhasma in the range of 0 to 2 wt %, Loha Bhasma in the range of 2 to 4 wt % and Swarna Makshika Bhasma in the range of 0 to 2 wt %.

The disclosed formulation, in the various embodiments herein, may further include a suitable excipient. The suitable excipients include solvents, binders, lubricants, herbal carriers, oils and salts that are generally known in the art. In a preferred embodiment, the excipient includes *acacia* gum.

Further, the amount of herb component and mineral component that may be included in the various embodiments of the disclosed formulation may be in the range of 0 to 10 wt %. In an embodiment, the formulation includes *Withania somnifera* (6 to 10 wt %), *Sida* (6 to 10 wt %), *Asparagus racemosus* (4 to 8 wt %), *Tinospora cordifolia* (4 to 8 wt %), *Moringa oleifera* (4 to 8 wt %), *Picrorhiza kurroa* (4 to 8 wt %), *Ocimum sanctum* (4 to 8 wt %), *Curcuma longa* (5 to 9 wt %) and Shilajit (4 to 8 wt %). In another embodiment, the formulation includes *Withania somnifera* (6 to 10 wt %), *Sida* (6 to 10 wt %), *Asparagus racemosus* (4 to 8 wt %), *Tinospora cordifolia* (4 to 8 wt %), *Moringa oleifera* (4 to 8 wt %), *Picrorhiza kurroa* (4 to 8 wt %), *Ocimum sanctum* (4 to 8 wt %), *Curcuma longa* (5 to 9 wt %), Abhraka Bhasma (2 to 4 wt %), Trivanga Bhasma (0 to 2 wt %), Pravala Bhasma (0 to 2 wt %), Loha Bhasma (2 to 4 wt %) and Swarna Makshika Bhasma (0 to 2 wt %). %). Further, in another embodiment, the formulation includes *Withania somnifera* (6 to 10 wt %), *Sida* (6 to 10 wt %), *Asparagus racemosus* (4 to 8 wt %), *Tinospora cordifolia* (4 to 8 wt %), *Moringa oleifera* (4 to 8 wt %), *Picrorhiza kurroa* (4 to 8 wt %), *Ocimum sanctum* (4 to 8 wt %), *Curcuma longa* (5 to 9 wt %), shilajit (4 to 8 wt %), Abhraka Bhasma (2 to 4 wt %), Trivanga Bhasma (0 to 2 wt %), Pravala Bhasma (0 to 2 wt %), Loha Bhasma (2 to 4 wt %) and Swarna Makshika Bhasma (0 to 2 wt %).

Further, the amount of gum *acacia* may be any amount suitable to perform the activity of an excipient. In an embodiment, the formulation may include gum *acacia* in the range of 0 to 50 mg per 500 mg of the formulation, preferably 10 wt %.

However, it is apparent that slight variations in the amount of the ingredients may be performed without otherwise deterring from the intended function of the herbo-mineral formulation.

The herbo-mineral formulation disclosed herein may be formulated in various dosage forms such that it is suitable for oral administration. The herbo-mineral formulation may be in the form of tablets, pellets, lozenges, granules, capsules, solutions, emulsions, suspensions, or any other form suitable for use. In an embodiment, the herbo-mineral formulation is formulated in the form of tablets, preferably 500 mg tablets. For example: Table 1 depicts the quantities of each ingredient in a 500 mg tablet.

Further disclosed herein, is a tablet for treating cancer. In an embodiment, the tablet is a 500 mg tablet having herb component, mineral component and excipient as depicted in Table 1.

TABLE 1

Each 500 mg tablet includes:

| Sl. No | Sanskrit Name | Part used | Latin/English name | Quantity |
|---|---|---|---|---|
| 1. | Ashvagandha | Dried root | *Withania somnifera* | 40 mg |
| 2. | Bala | Dried root | *Sida cordifolia* | 40 mg |
| 3. | Hareetakee | dry fruits | *Terminalia chebula* | 20 mg |
| 4. | Vibhitaki | dried fruits | *Terminalia bellerica* | 20 mg |
| 5. | Amalaki | dried fruits | *Emblica officinalis* | 20 mg |
| 6. | Shilajatu | Fossil resin | *Asphaltum punjabicanum* | 30 mg |
| 7. | Shatavari | Dried root | *Asparagus racemosus* | 30 mg |
| 8. | Guduchi | Dried stem | *Tinospora cordifolia* | 30 mg |
| 9. | Pippali | Dried fruit | *Piper longum* | 20 mg |
| 10. | Maricha | Dried fruit | *Piper nigrum* | 20 mg |
| 11. | Shunthi | Dried rhizome | *Zingiber officinalis* | 20 mg |
| 12. | Shigru | Dried stem bark | *Moringa oleifera* | 30 mg |
| 13. | Katuki | Dried root | *Picrorhiza kurroa* | 30 mg |
| 14. | Tulasi | Dried leaves | *Ocimum sanctum* | 30 mg |
| 15. | Haridra | Dried rhizome | *Curcuma longa* | 35 mg |
| 16. | Trivanga Bhasma | Incinerated tin, lead and zinc | Stanni-plumbi et Zinc oxidum | 5 mg |
| 17. | Swarna Makshika bhasma | Incinerated copper pyrite | Oxidum copper pyrite | 5 mg |
| 18. | Abhraka Bhasma | Incinerated mica | Mica oxidum | 10 mg |
| 19. | Loha bhasma | Mineral | Incinerated Iron (ferric oxide) | 10 mg |
| 20. | Pravala bhasma | Mineral | Coral calx (calcium carbonate) | 5 mg |
| 21. | Excipient | Gum | Gum *acacia* | 50 mg |

TABLE 2

| Drug powder with different reagents | Colour change in daylight/visible | Colour in ultra violet light |
|---|---|---|
| Drug powder as such | Brown | Pale green |
| Drug powder + $H_2O$ | Brown | Pale green |
| Drug powder + Alcohol | Brown | Black |
| Drug powder + 10% NaOH | Black | Dark green |
| Drug powder + $H_2SO_4$ | Brown | Black |
| Drug powder + $HNO_3$ | Brick red | Dark green |
| Drug powder + HCl | Brown | Black |

Example (2)

Physico-chemical investigation: Physicochemical investigations like Ash values in terms of total ash, acid insoluble ash value and water soluble ash value, pH values, tablet hardness test, disintegration time and water soluble extractive values, alcohol soluble extractive value and chloroform soluble extractive values are analyzed as per the parameters given in Indian Pharmacopeia of Ayurveda. pH Value of the drug was determined by checking the pH of the 1% drug solution prepared in distilled water using Systronics digital pH Meter MKVI. The tablet disintegration time was checked with the help of Tablet disintegration machine (I.P.ST-D.ROTEK) and Tablet hardness tester (SECOR.INDIA) used to find out the hardness of the tablet. Each experiment was repeated thrice.

Table 3 depicts the results of Physiochemical analysis of the drug such as Total ash, acid insoluble ash value, water soluble ash value, alcohol soluble extractive value, water soluble extractive value, chloroform soluble extractive value, pH Value, hardness test and disintegration time of the tablet. The percentage of loss on drying was found to be very less i.e. 2.44%. This could maintain the drug for long use without the attack of microorganisms. Percentage of moisture content for crude drug is not more than 14%. Evaluation of ash value is also important in maintaining the purity and quality of the drugs. High ash value shows the presence of contamination, substitution or the presence or absence of foreign inorganic matter such as metallic salts or/and silica.

Embodiments of the disclosed herbo-mineral formulation (also referred to as 'drug' or 'test drug') in tablet form was analyzed for fluorescent behavior, phytoconstituents, physiochemical properties etc. The analysis and results obtained are included hereunder as examples by way of illustration only and should not be construed to limit the scope of the claims provided herewith. It will be apparent to those skilled in the art that many modifications, both to materials and methods, may be practiced without departing from the scope of the claims.

Example (1)

Fluorescent behavior: Powdered drug was dissolved in different chemical reagents and organic reagents such as alcohol, 50% sulphuric acid, 10% sodium hydroxide, 50% nitric acid and water and subjected to analysis under UV light. Table 2 depicts the florescent behavior of the drug. Drug showed varying colors in UV and visible lights.

Ash value of the test drug is not too high. Total ash value found to be 18%, acid insoluble ash is 1.2% and water soluble ash is 16.5%. The alcohol extractive value, water soluble extractive value and chloroform extractive value found to be 6.4%, 4.4% and 9.36% respectively. The other important physical parameters like tablet disintegration time, tablet hardness test, uniformity of weight and pH Value were 3-5 minutes, 4 kg/cm, 500 mg and 6.1 respectively.

TABLE 3

| Drug powder with different reagents | Colour change in daylight/visible |
|---|---|
| Loss on drying | 2.44% |
| Tablet disintegration test | 3-5 minutes |
| Tablet Hardness test | 4.0 kg/cm |
| Uniformity of weight | 500 mg |
| pH value | 6.1 |
| Total ash content | 18% |
| Acid insoluble ash value | 1.2% |
| Water soluble ash value | 16.5% |
| Alcohol extractive value | 6.4% |
| Water soluble extractive value | 4.4% |
| Chloroform soluble extractive value | 9.36% |

Example (3)

Phytochemical study: Chemical analysis was done for the screening of components like ferrous iron, ferric iron, lead, copper, sulphur, etc. Qualitative tests were also employed to screen the various phyto constituents/secondary metabolites such as glycosides, steroids, saponins, proteins, tannins etc.

Table 4 depicts the results of Qualitative analysis performed for phytoconstituents and other components. Its phytoconstituents showed the presence of alkaloids, steroids, glycosides and different components like, ferrous iron, ferric iron and sulphur which could make the drug potential in curing diseases.

TABLE 4

| Name test for | Results |
|---|---|
| Alkaloids | + |
| Tannins | + |
| Saponins | − |
| Steroids | − |
| Carbohydrates | + |
| Proteins | + |
| Ferrous iron | + |
| Ferric iron | + |
| Lead | − |
| Copper | − |
| Sulphur | + |

(+) denotes presence and (−) denotes absence

Example (4)

HPTLC analysis was performed on precoated silica gel 60F 254 aluminum packed HPTLC plates (Merck) to a band width of 6 mm using Linomat 5 TLC applicator. The plate was developed in Toluene:Ethyl acetate (9:1) and the developed plates were visualized and scanned under UV 254, 366, and after derivatization in vanillin-sulphuric acid spray reagent at 620 nm. Rf, colour of the spots, densitometric scan and superimposability of densitogram were recorded. The mobile phase was Toluene: Ethyl acetate (9:1). After drying the spots in a current of air the plates were placed in one trough of Camag twin trough glass chamber. The mobile phase was poured into the chamber left to equilibrate for 30 min. the plate was then developed until the solvent front had traveled a distance of 7 cm and 12 cm above the position of sample application. The plate was removed from the chamber and dried in a current of air. Detection was performed with a Camag TLC Scanner. Photo documentation was done at 254 and 366 nm.

FIG. 3(a) through 3(f) depicts the results of HPTLC analysis, wherein Track 1—Amalaki; Track 2—Aswagandha; Track 3—Bala; Track 4—Bhrangaraja; Track 5—Iswari; Track 6—Haridra; Track 7—Haritaki; Track 8—Kancanara; Track 9—Marica; Track 10—Nimba; Track 11—Pippali; Track 12—Punarnava; Track 13—Tulasi; Track 14—Sigru; Track 15—Sunthi; Track 16—Vasa; Track 17—Vibhitaki; Track 18—Drug. FIG. 3(a), 3(b), 3(c), 3(d), 3(e) and 3(f) are illustration of the results of the TLC analysis under UV light (7 cm) at UV 254, UV light (7 cm) at UV 366, under white light, under UV light (12 cm), UV light (12 cm) at UV 254 and UV light (12 cm) at UV 366, respectively.

The HPTLC finger printing of the product revealed the presence of similar bands with all its ingredients. The color of the band fluorescent green with Rf value 0.07. This particular band is present in all other 17 ingredients of this drug. The product showed the presence of 7 bands with Rf value 0.03, 0.07, 0.09, 0.12, 0.72, 0.81, 0.88 with fluorescent green, fluorescent Yellow, fluorescent yellow, fluorescent Yellow, fluorescent green, fluorescent Violet, fluorescent blue respectively.

The Rf values of its ingredients and the product having compatible Rf values with similar color. Each Rf value denotes specific constituents of the drugs. The chemical fingerprints of the drugs could be used as a reference standard for further quality control assessment.

Table 5 depicts the Rf (retardation factor) values of various ingredients and the drug disclosed herein, wherein FB—Fluorescent blue; FV—Fluorescent violet; FP—Fluorescent pink; FY—Fluorescent yellow and FG—Fluorescent green.

TABLE 5

| T1 | T2 | T3 | T4 | T5 | T6 | T7 | T8 | T9 | T10 | T11 | T12 | T13 | T14 | T15 | T16 | T17 | T18 |
|---|---|---|---|---|---|---|---|---|---|---|---|---|---|---|---|---|---|
| — | — | — | 0.02 FP | — | — | — | — | — | — | — | 0.02 FP | — | — | — | — | 0.02 FY | — |
| — | — | — | — | 0.03 FB | — | — | — | — | — | — | — | — | — | — | — | — | 0.03 FG |
| — | — | — | — | — | — | — | 0.04 FB | 0.04 FV | — | — | — | — | — | — | 0.04 FV | — | — |
| — | — | — | 0.05 FP | — | — | — | — | — | — | — | — | — | — | — | — | — | — |
| 0.07 FB | 0.07 FB | 0.07 FP | 0.07 FB | — | — | — | — | — | — | — | 0.07 FP | — | — | — | — | 0.07 FY | 0.07 FY |
| — | — | — | — | — | — | — | 0.08 FB | — | — | — | — | — | — | — | — | — | — |
| — | — | — | — | — | — | — | — | — | — | — | — | — | — | — | — | — | 0.09 |

TABLE 5-continued

| T1 | T2 | T3 | T4 | T5 | T6 | T7 | T8 | T9 | T10 | T11 | T12 | T13 | T14 | T15 | T16 | T17 | T18 |
|---|---|---|---|---|---|---|---|---|---|---|---|---|---|---|---|---|---|
| — | — | — | — | — | — | — | 0.1 FB | — | 0.1 FB | — | — | — | — | — | — | — | FY |
| — | — | — | 0.11 FF | 0.11 FB | — | — | — | — | — | — | — | — | — | — | — | — | — |
| — | — | — | — | — | — | — | — | 0.12 FV | — | — | — | — | 0.12 FB | — | — | — | 0.12 FY |
| — | — | — | — | — | — | — | — | — | — | — | — | — | — | — | — | 0.13 FY | — |
| — | — | — | — | — | — | — | 0.15 FY | — | — | — | — | — | — | — | — | — | — |
| — | — | — | — | — | — | — | — | — | — | — | — | — | — | — | — | — | 0.17 FB |
| — | — | — | 0.19 FP | — | 0.19 FV | 0.19 FV | — | — | — | — | — | — | — | — | — | — | — |
| — | — | — | — | — | — | — | — | — | — | — | — | — | 0.21 FB | — | — | — | — |
| — | — | — | — | — | — | — | — | — | — | — | 0.27 FP | — | — | — | — | — | — |
| — | — | — | — | — | — | — | — | 0.29 FV | — | — | — | — | — | — | 0.29 FP | — | — |
| — | — | 0.30 FP | — | — | — | — | — | — | — | — | — | — | — | — | — | — | — |
| — | — | — | — | — | — | — | — | — | — | FP | 0.32 FP | — | — | — | — | — | — |
| — | — | — | — | — | — | — | — | — | — | — | — | — | — | — | — | — | 0.33 FV |
| — | — | — | — | — | — | — | — | — | — | — | — | — | — | — | 0.34 FP | — | — |
| — | — | — | 0.39 FB | 0.39 FB | 0.39 FB | — | 0.39 FB | 0.39 FB | — | — | — | — | — | — | — | — | — |
| — | 0.40 FB | 0.40 FB | — | — | — | 0.40 FB | — | — | 0.40 FB | 0.40 FB | 0.40 FB | — | — | — | — | — | — |
| — | — | — | — | — | — | — | — | — | — | — | — | 0.41 FB | — | — | — | — | — |
| — | — | — | — | — | — | — | — | — | — | — | — | — | 0.42 FB | 0.42 FB | — | — | — |
| — | — | — | — | — | — | — | — | — | — | — | — | — | — | — | 0.43 FB | — | — |
| — | — | — | — | — | — | — | — | — | — | — | — | — | — | — | — | 0.44 FB | 0.44 FB |
| — | — | — | — | — | — | — | — | — | — | — | — | — | — | — | 0.46 FP | — | — |
| — | — | 0.49 FP | — | — | — | — | — | — | — | — | — | — | — | — | — | — | — |
| — | — | — | — | — | — | — | — | — | — | — | 0.50 FP | — | — | — | — | — | — |
| — | — | — | — | — | — | — | — | — | — | — | — | — | — | — | 0.53 FP | — | — |
| — | — | — | 0.68 FG | — | — | — | — | — | — | — | — | — | — | — | — | — | — |
| — | — | — | — | — | — | — | — | — | — | — | — | — | — | — | — | — | 0.72 FG |
| — | — | — | — | — | — | 0.74 FV | 0.74 FV | — | — | 0.74 FV | — | — | — | — | — | — | — |
| — | — | — | — | 0.75 FV | — | — | — | 0.75 FV | 0.75 FV | — | 0.75 FV | — | — | — | — | — | — |
| — | — | — | — | — | — | — | — | — | — | — | — | — | 0.76 FV | — | 0.76 FV | — | — |
| — | — | — | — | — | — | — | — | — | — | — | — | — | — | 0.77 FV | — | — | — |
| — | — | — | 0.78 FV | — | — | — | — | — | — | — | — | — | — | — | — | 0.78 FV | — |
| — | — | — | — | — | — | — | — | — | — | — | — | — | — | — | — | — | 0.81 FV |
| — | — | — | 0.86 FV | — | — | — | — | — | — | — | — | — | — | — | — | — | — |
| — | — | — | — | — | — | — | — | — | — | — | — | — | — | — | — | — | 0.88 FB |

FB—Fluorescent blue;
FV—Fluorescent violet;
FP—Fluorescent pink;
FY—Fluorescent yellow;
FG—Fluorescent green Method Disclosed herein are embodiments of a method of preparing the herbo-mineral formulation. In an embodiment, the method includes, levigating bhasmas and shilajit in a grinder;
    adding finely powdered herbs into the grinder; and
    adding grinding decoction while continuing grinding to obtain a ground mass.

The bhasmas include at least one of Abhraka Bhasma, Trivanga Bhasma, Pravala Bhasma, Loha Bhasma and Swarna Makshika Bhasma. The mixture of bhasmas and Shilajit may be in semi solid form. In an embodiment, the levigation may be performed for a duration of around 3 hours.

Further, the finely powdered herbs include finely powdered *Withania somnifera* (Dried root), *Sida cordifolia* (Dried root), *Terminalia chebula* (Dry fruits), *Terminalia bellerica* (Dried fruits), *Emblica officinalis* (Dried fruits), *Asparagus racemosus* (Dried root), *Tinospora cordifolia* (Dried stem), *Piper longum* (Dried fruit), *Piper nigrum* (Dried fruit), *Zingiber officinalis* (Dried rhizome), *Moringa oleifera* (Dried stem bark), *Picrorhiza kurroa* (Dried root), *Ocimum sanctum* (Dried leaves), *Curcuma longa* (Dried rhizome). In an embodiment, finely powdered herbs may be obtained by powdering and sieving the herb components at 80 mesh.

The grinding decoction is a decoction of selected herbs (also referred as grinding herbs). In an embodiment, the grinding decoction is a decoction of one or more herbs selected from a group consisting of: *Aegle marmelos, Premna mucronata, Oroxylum indicum, Stereospermum suaveolens, Gmelina arborea, Solanum indicum, Solanum xanthocarpum, Tribulus terrestris, Uraria picta, Desmodium gangeticum, Vinca rosea, Semecarpus anacardium, Asparagus racemosus, Momordica charantia, Acacia catechu, Ocimum sanctum, Rubia cordifolia, Bauhinia variegate, Adhatoda vasica, Eclipta alba, Moringa oleifera, Cynodon dactylon, Tinospora cordifolia, Crotalaria juncea, Cuminum cyminum, Smilax china, Mimosa pudica, Calotropis procera, Sida rhombifolia, Murraya koenigii* and *Trichosanthes dioica*.

The decoction may be obtained by any method of decocting generally known in the field. In an embodiment, the method of preparation of grinding decoction includes, soaking the grinding herbs. For example, soaking powdered dried roots of *Aegle marmelos, Premna mucronata, Oroxylum indicum, Stereospermum suaveolens, Gmelina arborea, Solanum indicum, Solanum xanthocarpum, Uraria picta, Calotropis procera, Sida rhombifolia, Desmodium gangeticum, Moringa oleifera* and *Rubia cordifolia, Asparagus racemosus*; dried fruit of *Tribulus terrestris*; fresh whole plant of *Vinca rosea, Cynodon dactylon, Crotalaria juncea, Eclipta alba* and *Momordica charantia*; purified fruit of *Semecarpus anacardium*; dried heartwood of *Acacia catechu*, fresh leaves of *Ocimum sanctum, Murraya koenigii* and *Adhatoda vasica*; dried stem bark of *Bauhinia variegate* and *Moringa oleifera*; fresh stem of *Tinospora cordifolia*; dried *cremocarp* of *Cuminum cyminum*; dried bulb of *Smilax china*; dried whole plant of *Mimosa pudica* and *Trichosanthes dioica*; and concentrating the soaked herb mixture.

In an embodiment, soaking may be performed by soaking the grinding herbs in 16 parts of water overnight. In a further embodiment, concentrating may be performed by boiling at high temperature, preferably about 80° C. to 85° C., until ⅛th of the liquid remains. Concentration may be confirmed with the help of Brix meter.

Figure 2:
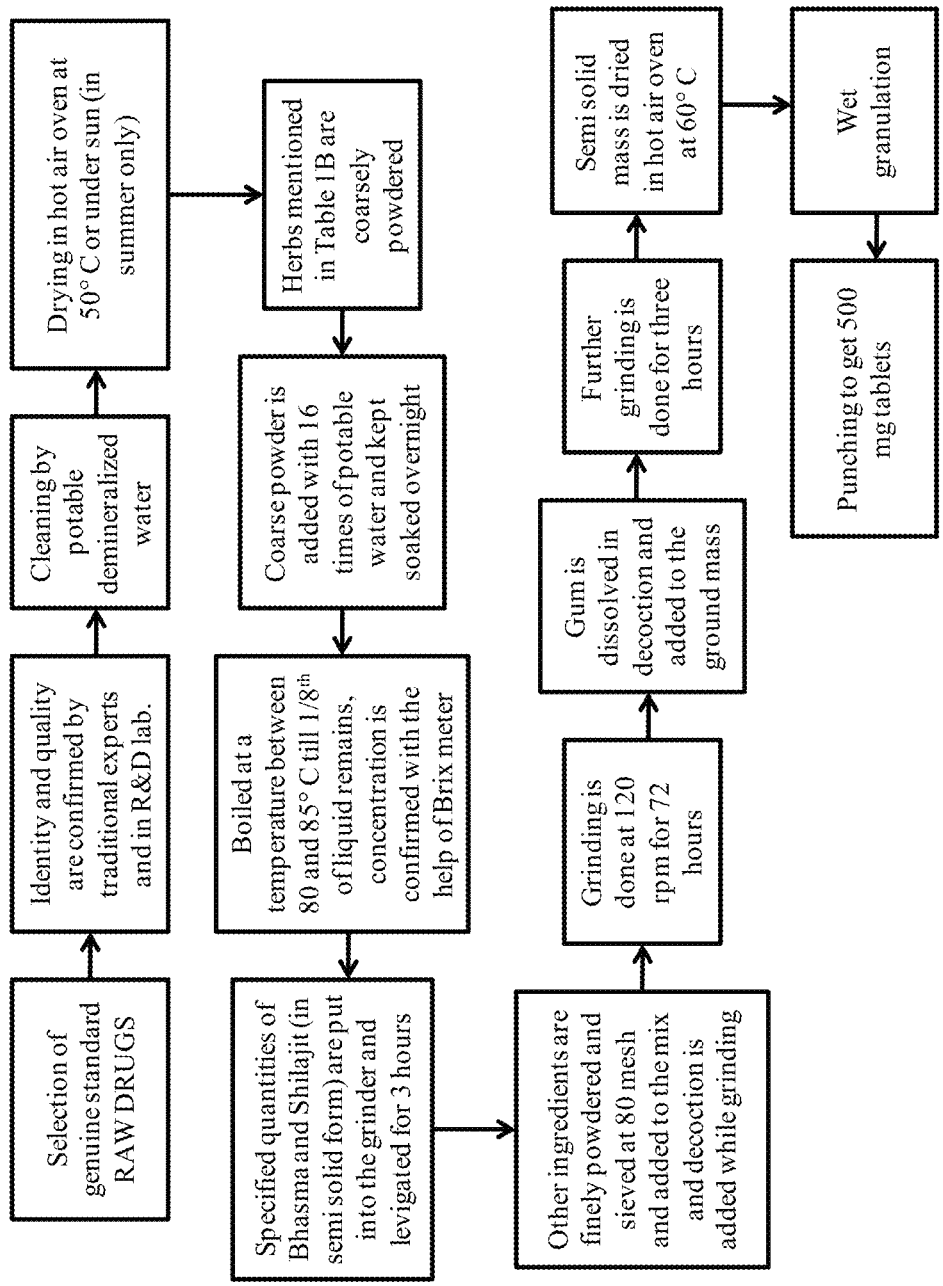
FIG. 2 depicts a flowchart for the preparation of fortified tablets.
Figure 3A:
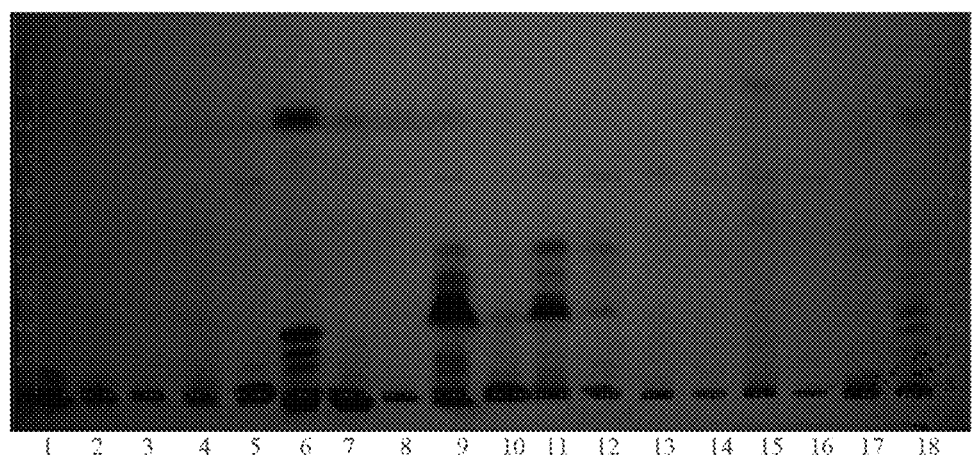
FIG. 3(*a*) is an illustration of the results of the TLC analysis under UV light (7 cm), at UV 254.
Figure 3B:
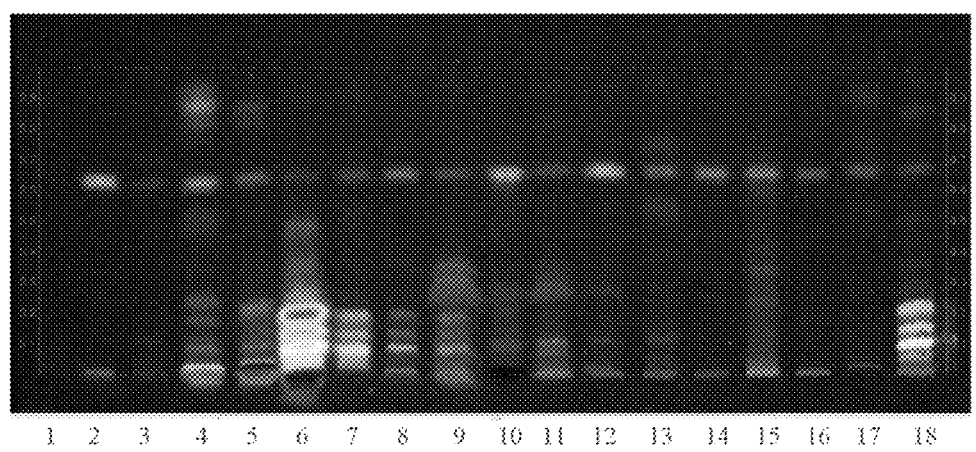
Figure 3C:
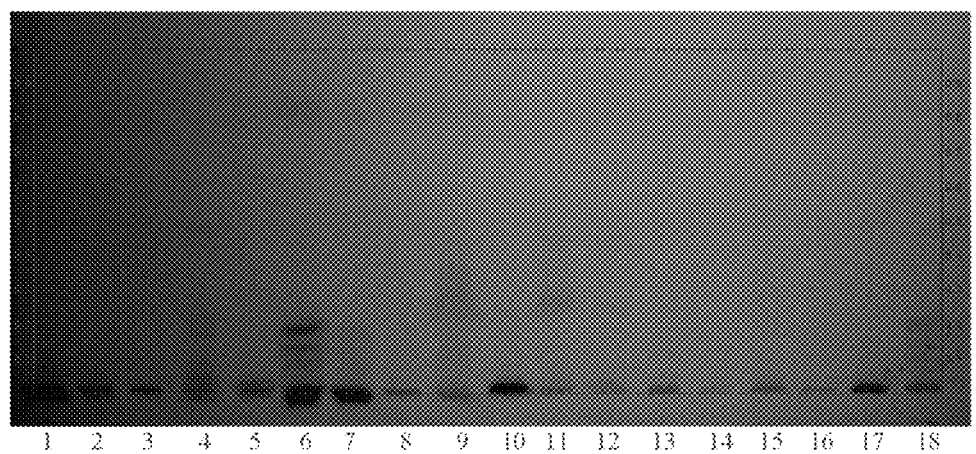
Figure 3D:
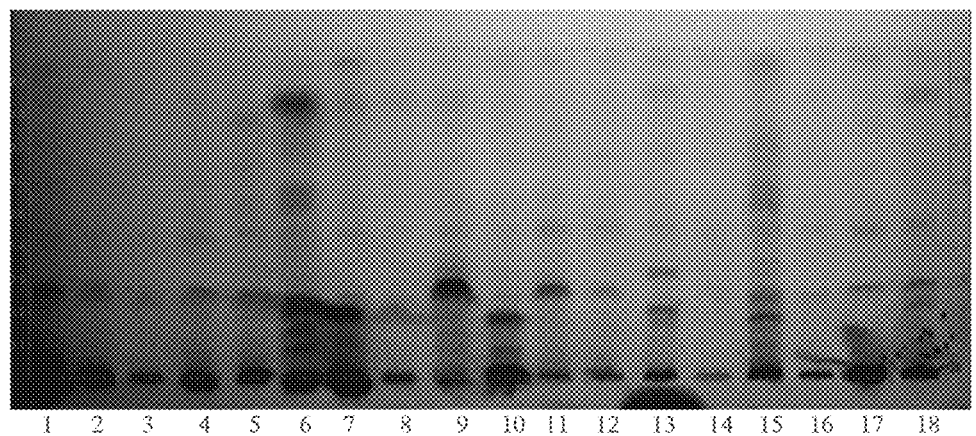
Figure 3E:
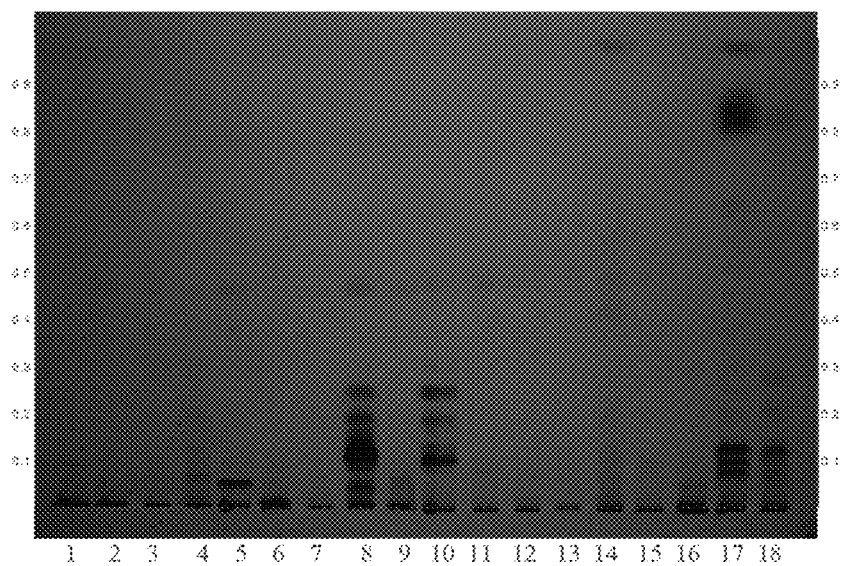
Figure 3F:
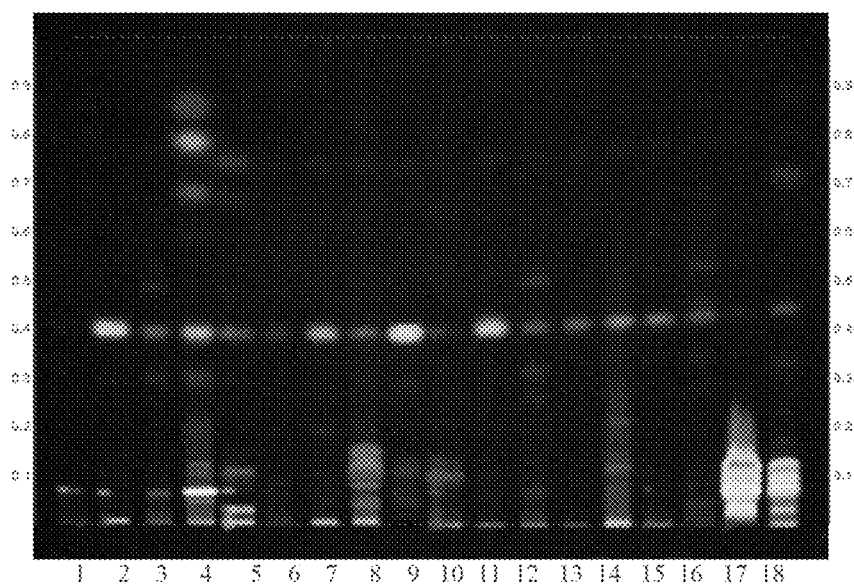

Further, once the grinding decoction is added, grinding is continued. In an embodiment, grinding is continued for about 72 hours, preferably at 120 rpm, to obtain a ground mass. In an embodiment, the method of preparation may further include adding excipient to the ground mass, wherein gum *acacia* may be added to the ground mass by dissolving in the grinding decoction while continuing grinding for 3 hours to obtain a semisolid mass. The method of preparation may further include drying at 50° C.-60° C., preferably in a hot air oven, wet granulating, punching to obtain 500 mg tablets. FIG. 2 depicts a flowchart for the preparation of fortified tablets. Table 6 depicts an embodiment of the Herbs required for grinding (grinding herbs).

TABLE 6

| | | Decoction of following herbs: | |
|---|---|---|---|
| 1. | Bilva dried root | *Aegle marmelos* | 1 part |
| 2. | Agnimantha dried root | *Premna mucronata* | 1 part |
| 3. | Shyonaka dried root | *Oroxylum indicum* | 1 part |
| 4. | Patala dried root | *Steriospermum suaveolens* | 1 part |
| 5. | Gambhari dried root | *Gmelina arborea* | 1 part |
| 6. | Brihati dried root | *Solanum indicum* | 1 part |
| 7. | Kantakari dried root | *Solanum xanthocarpum* | 1 part |
| 8. | Gokshura dried fruit | *Tribulus terrestris* | 1 part |
| 9. | Prishniparni dried root | *Uraria picta* | 1 part |
| 10. | Shalaparni dried root | *Desmodium gangeticum* | 1 part |
| 11. | Sadapushpa fresh whole plant | *Vica rosea* | 1 part |
| 12. | Bhallataka purified fruit | *Semecarpus anacardium* | 1 part |
| 13. | Shatavari dried root | *Asparagus racemosus* | 1 part |
| 14. | Karavellaka fresh whole plant | *Momordica charantia* | 1 part |
| 15. | Khadira dried heartwood | *Acacia catechu* | 1 part |
| 16. | Tulasi fresh leaves | *Ocimum sanctum* | 1 part |
| 17. | Manjishtha dried root | *Rubia cordifolia* | 1 part |
| 18. | Kanchanara dried stem bark | *Bauhinia variegata* | 1 part |
| 19. | Vasa frsh leaves | *Adhatoda vasica* | 1 part |
| 20. | Bhrngaraja fresh whole plant | *Eclipta alba* | 1 part |
| 21. | Shigru dried stem bark | *Moringa oleifera* | 1 part |
| 22. | Shigru dried root | *Moringa oleifera* | 1 part |
| 23. | Durva fresh whole plant | *Cynodon dactylon* | 1 part |
| 24. | Guduchi fresh stem | *Tinospora cordifolia* | 1 part |

TABLE 6-continued

| | Decoction of following herbs: | | |
|---|---|---|---|
| 25. | Shanapushpi fresh whole plant | *Crotolaria juncea* | 1 part |
| 26. | Jeeraka dried cremocarp | *Cuminum cyminum* | 1 part |
| 27. | Madhusnuhi dried bulb | *Smilax china* | 1 part |
| 28. | Lajjalu dried whole plant | *Mimosa pudica* | 1 part |
| 29. | Arka dried root | *Calotropis procera* | 1 part |
| 30. | Bala dried root | *Sida rombifolia* | 1 part |
| 31. | Kaidarya fresh leaves | *Murraya koeinigi* | 1 part |
| 32. | Patola dried whole plant | *Trichosanthus dioica* | 1 part |
| | Jala | Water | 512 pats |
| | Avashesha (Reduced to) | | ⅛ part of water |

The bhasmas that are used in the various embodiments of the disclosed herbo-mineral formulation may be prepared by methods that are generally known in the field. In an embodiment, bhasmas may be prepared by selecting genuine standard minerals as starting material such as Swarna makshika, Mica, Iron, etc; drying in a hot air oven; purifying the mineral by triturating, quenching, boiling, etc; triturating with herbal decoction; preparing into discs; drying of discs; preparing Sharavasam puta, subjecting Sharavasam puta to Gaja puta, and powdering of discs once cooled. In an embodiment, the method is repeated 30 times till bhasma is obtained.

Figure 1B:
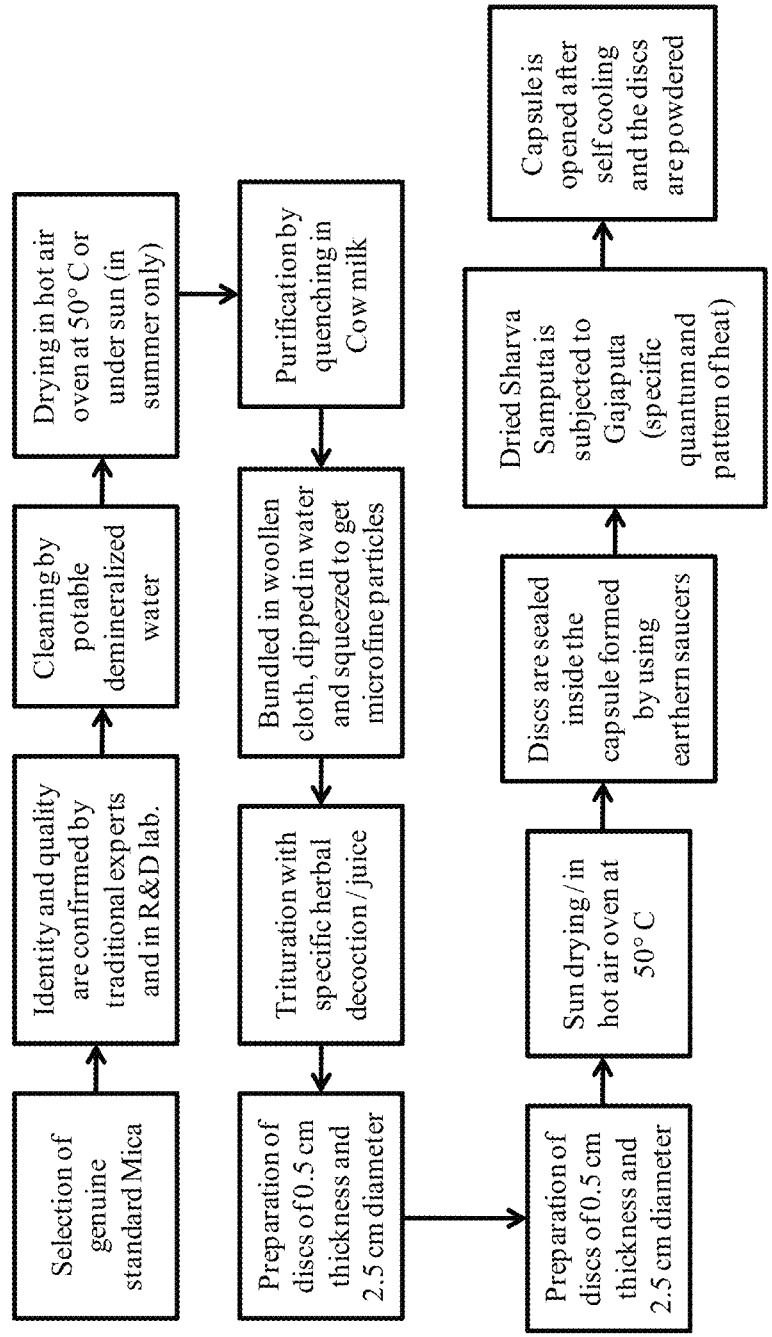
Figure 1C:
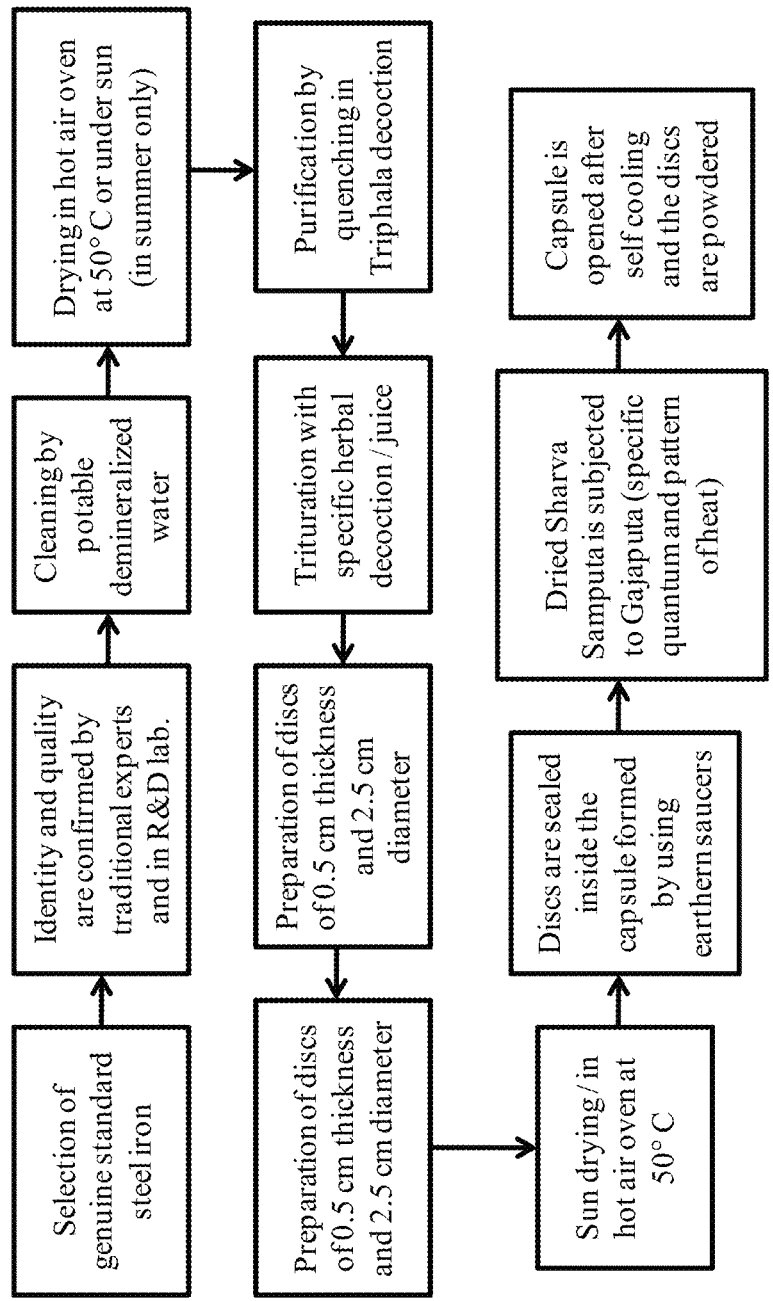
Figure 1D:
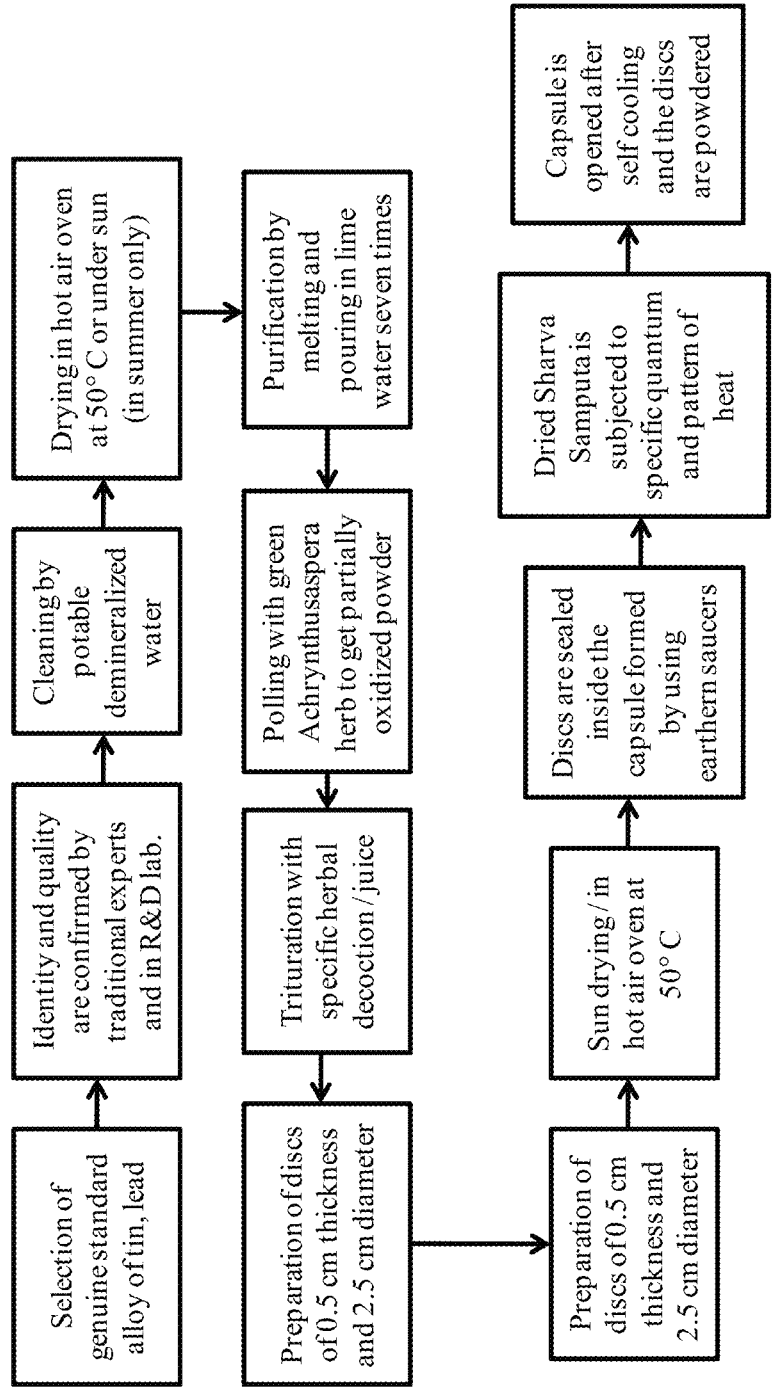
Figure 1E:
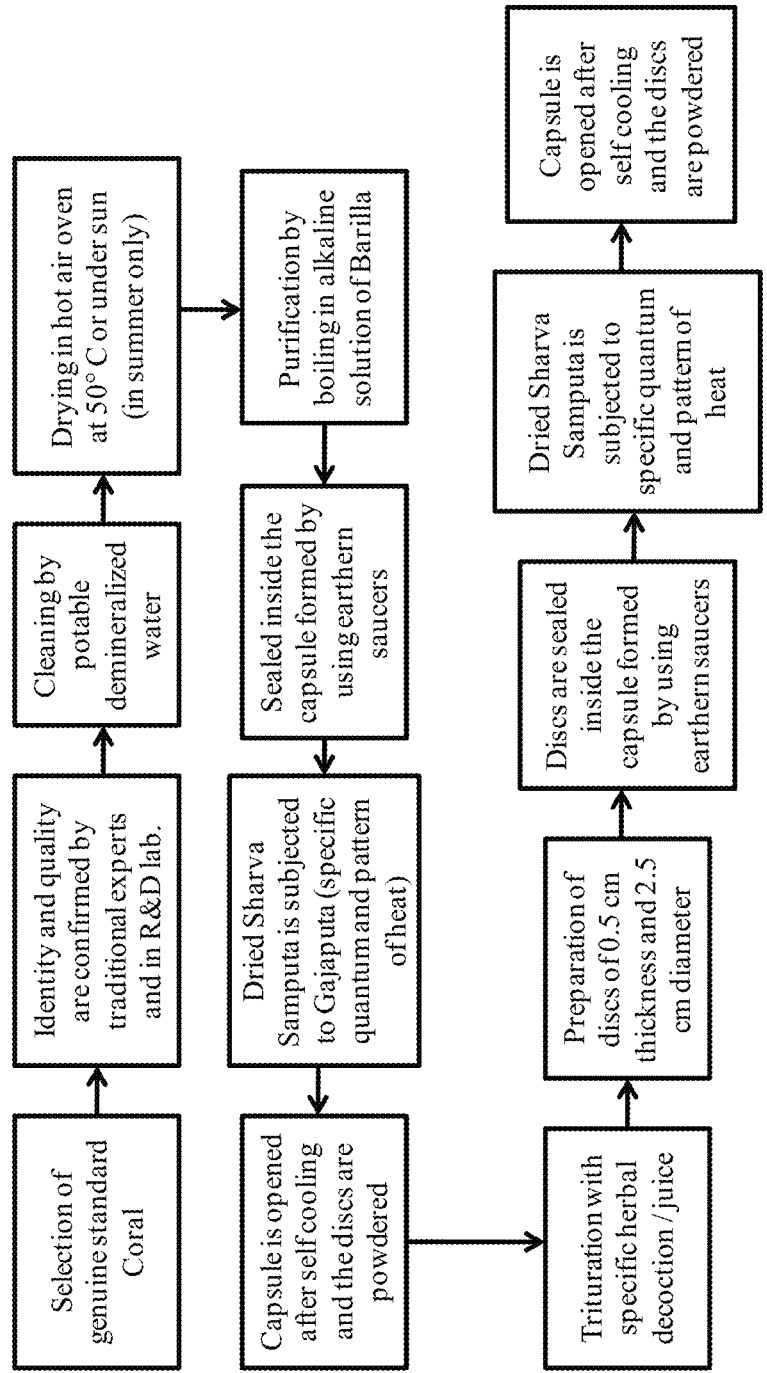

The starting materials used in the preparation of bhasmas may include standard minerals generally used in the field. In an embodiment, the preparation of Swarna Makshika Bhasma includes swarna makshika as the starting material. FIG. 1(a) depicts a flowchart for the preparation of Swarna Makshika Bhasma using swarna makshika as the starting material. In an embodiment, the preparation of Abhraka Bhasma includes Mica as the starting material. FIG. 1(b) depicts a flowchart for the preparation of Abhraka Bhasma using Mica as the starting material. In an embodiment, the preparation of Loha Bhasma includes steel iron as the starting material. FIG. 1(c) depicts a flowchart for the preparation of Loha Bhasma using steel iron as the starting material. In another embodiment, the preparation of Trivanga Bhasma includes alloys of Tin and lead as the starting material. FIG. 1(d) depicts a flowchart for the preparation of Trivanga Bhasma using alloys of Tin and lead as the starting material. In an embodiment, the preparation of Pravala Bhasma includes Coral as the starting material. FIG. 1(e) depicts a flowchart for the preparation of Pravala Bhasma using Coral as the starting material.

The purification, or shodhana, of the mineral may be performed by generally known methods in the field. In an embodiment, the purification may be by mixing the mineral, such as swarna makshika, with rocksalt and lemon juice and heating strongly till partially oxidized into reddish powder which may further be used in the preparation of Swarna makshika Bhasma. In another embodiment, the purification may be by quenching a mineral such as mica in Cow's milk, wherein it is further used in the preparation of Abhraka Bhasma.

In yet another embodiment, the purification may be by quenching a mineral such as steel iron in Triphala decoction, which is further used in the preparation of Loha Bhasma. In yet another embodiment, the purification may be by melting and pouring a mineral such as an alloy of tin and lead in lime water, preferably seven times, which is further used in the preparation of Trivanga Bhasma.

Further, in an embodiment, the process of purification may include boiling mineral such as Coral in an alkaline solution of Barilla, which is further used in the preparation of Pravala Bhasma.

The herbal decoction used may be any herbal decoction that is generally used for triturating in the preparation of bhasmas. In an embodiment, the herbal decoction includes one of more herbal ingredient selected from a group consisting of Nimbu Swarasa (Lemon juice) and Kulatha Kwatha (Decoction of *Dolichos biflorus*), wherein it is useful in the preparation of Swarna Makshika bhasma. In another embodiment, the herbal decoction specifically includes Arka Ksheera (Latex of *Calotropis procera*), Snuhi Ksheera (Latex of *Euphorbia neriifolia*), Vata Ksheera (Latex of *Ficus benghalensis*), Kakamachi Rasa (fresh juice of *Solanum nigrum* whole plant), Gokshura Kwatha (decoction of *Tribulus terrestris* fruits), Apamarga Rasa (Juice of Achyranthes *aspera* plant), Vata Praroha Swarasa (juice of aerial root of *Ficus benghalensis*), Gomutra (Cow urine), Tulasi Swarasa (Fresh juice of *Ocimum sanctum* leaves), Kadali Shipha Jala (Juice of plantain rhizome), Eranda patra rasa (Juice of *Ricinus communis* leaves), and Guda (Jaggery), wherein it is useful in the preparation of Abhraka Bhasma. In an embodiment, the herbal decoction specifically includes Triphala Kashaya (decoction of fruits of *Terminalia chebula*, *Terminalia bellerica* and *Emblica officinalis*), wherein it is useful in the preparation of Loha Bhasma.

Treatment

Disclosed herein are embodiments of a method of treating cancer. The embodiments disclosed herein may be used to improve the general health of individuals having a condition involving abnormal, unregulated cell proliferation. Also disclosed are embodiments of a method of inducing cancer cell cytotoxicity and apoptosis. Further, the embodiments disclosed include a method of inducing antiproliferative and growth inhibitory effect on cancerous cells.

In an embodiment, the method includes administering to a patient a composition as described in any of the embodiments disclosed herein.

In an embodiment, the patient may be any individual in need of such treatment including ones having/expected or suspected of having cancer, tumor, cancer associated complications etc. Further, the patient may also be any individual having a condition involving abnormal, unregulated cell proliferation of any cell type including conditions such as carcinoma of esophagus, carcinoma of lung, bronchogenic carcinoma, adenocarcinoma of endometrium, adenocarcinoma of rectum, Non-Hodgkin's lymphoma, chronic myeloid leukemia, borderline mucinous tumor, adenocarcinoma of colon, fibro sarcoma, ovarian carcinoma, Cervix Adenocarcinoma, carcinoma of pancreas etc. Experimental studies show significant improvement in cases of Dalton Cell lymphoma. In a specific embodiment, the patient includes an individual having Dalton Cell lymphoma. The patient may further include individuals having undergone prior cancer treatment procedures such as chemotherapy, surgery, or no prior cancer treatment procedures. In another embodiment, the cancer cells include any cells that are cancerous in nature including Human Cervix Adenocarcinoma cells, Human Lung Carcinoma cells, Human Ovarian Cancer cells etc.

In an embodiment, the method of treating cancer includes administering to a patient a composition having a herb component, a mineral component and a suitable excipient, wherein the herb component includes a herb component of the following herbs *Withania somnifera* (6 to 10 wt %), *Sida* (6 to 10 wt %), *Asparagus racemosus* (4 to 8 wt %), *Tinospora cordifolia* (4 to 8 wt %), *Moringa oleifera* (4 to 8 wt %), *Picrorhiza kurroa* (4 to 8 wt %), *Ocimum sanctum* (4 to 8 wt %), *Curcuma longa* (5 to 9 wt %) and at least one herb selected from *Terminalia chebula*, *Terminalia bellerica*, *Emblica officinalis*, *Piper longum*, *Piper nigrum* and *Zingiber officinalis* (2 to 6 wt %); and the mineral component includes Shilajit (4 to 8 wt %) and at least one of Abhraka Bhasma (2 to 4 wt %), Trivanga Bhasma (0 to 2 wt %), Pravala Bhasma (0 to 2 wt %), Loha Bhasma (2 to 4 wt %) and Swarna Makshika Bhasma (0 to 2 wt %).

In an embodiment, the method of inducing cancer cell cytotoxicity/apoptosis and/or antiproliferative/growth inhibitory effect includes exposing cancer cells to a composition having a herb component and a mineral component, wherein the herb component includes a herb component of the following herbs *Withania somnifera* (6 to 10 wt %), *Sida* (6 to 10 wt %), *Asparagus racemosus* (4 to 8 wt %), *Tinospora cordifolia* (4 to 8 wt %), *Moringa oleifera* (4 to 8 wt %), *Picrorhiza kurroa* (4 to 8 wt %), *Ocimum sanctum* (4 to 8 wt %), *Curcuma longa* (5 to 9 wt %) and at least one herb selected from *Terminalia chebula*, *Terminalia bellerica*, *Emblica officinalis*, *Piper longum*, *Piper nigrum* and *Zingiber officinalis* (2 to 6 wt %); and the mineral component includes Shilajit (4 to 8 wt %) and at least one of Abhraka Bhasma (2 to 4 wt %), Trivanga Bhasma (0 to 2 wt %), Pravala Bhasma (0 to 2 wt %), Loha Bhasma (2 to 4 wt %) and Swarna Makshika Bhasma (0 to 2 wt %).

The disclosed method of treatment may be used as a primary line of treatment or as an adjunct to other cancer treatment methods. In an embodiment, the method may be instrumental in improving the health conditions of individuals having cancer.

The dosage of the test drug and the treatment regimen may vary depending on the patient. The disclosed formulation was evaluated for acute toxicity as per OECD (Organisation for Economic Co-operation and Development) guidelines 423 (Acute Class Method) and found to be safe and non-toxic even beyond 5000 mg/Kg body weight.

Embodiments of the formulation disclosed herein were analyzed for cytotoxicity against selected cell lines. Embodiments of the formulations disclosed herein (also referred to as test drug) is further described by reference to the following examples by way of illustration only, and should not be construed to limit the scope of the embodiments herein. The following examples disclose invitro analysis of embodiments of the disclosed formulation on selected cell lines. It will be apparent to those skilled in the art that many modifications, both to materials and methods, may be practiced without departing from the scope of the claims.

Example 5: In Vitro Anticancer Study of the Test Drug on Selected Cell Lines

Objective: The purpose of this Study was to evaluate the test substances for their cytotoxicity against selected cell lines.

Summary: In-vitro cytotoxicity of the test substances test drug was tested by MTT assay on A549 (Human Lung Carcinoma), and HeLa (Human Cervix Adenocarcinoma) cell lines. The test drug was taken at concentrations ranging from 1000 µg/ml to 7.8 µg/ml to determine the percentage growth inhibition on the cell lines A549, and HeLa. The test substances exhibited a CTC50 value of >1000, on both cell lines.

Method: The in-vitro cytotoxicity study was performed for test drug on A549 (Human Lung Carcinoma), and HeLa (Human Cervix Adenocarcinoma) cell lines. Cell lines to find toxic concentration of the tablets by MTT assay.

Preparation of test solution: For cytotoxicity studies, 10 mg of all the eight test substances were separately dissolved and volume was made up with MEM/DMEM-HG supplemented with 2% inactivated FBS to obtain a stock solution of 1 mg/ml concentration and sterilized by 0.22 syringe filtration. Serial two fold dilutions were prepared from this for carrying out cytotoxic studies.

Cell line and culture medium: A549 (Human Lung Carcinoma), and HepG2 (Human Liver Carcinoma) cell lines were procured from National Centre for Cell Sciences (NCCS), Pune, India. Stock cells were cultured in their respective media viz. MEM/DMEM-HG supplemented with 10% inactivated Fetal Bovine Serum (FBS), penicillin (100 IU/ml), streptomycin (100 µg/ml) and amphotericin B (5 µg/ml) in an humidified atmosphere of 5% $CO_2$ at 37° C. until confluent.

The cells were dissociated with TPVG solution (0.2% trypsin, 0.02% EDTA, 0.05% glucose in PBS). The stock cultures were grown in 25 $cm^2$ culture flasks and all experiments were carried out in 96 well microtiter plates (Tarsons India Pvt. Ltd., Kolkata, India).

Cytotoxicity studies: In all the cell lines, the monolayer cell culture was trypsinized and the cell count was adjusted to 100,000 cells/ml using respective media viz., MEM/DMEM-HG containing 10% FBS. To each well of the 96 well microtiter plate, 0.1 ml of the diluted cell suspension was added. After 24 h, when a partial monolayer was formed, the supernatant was flicked off, monolayer washed once with medium and 100 µl of different test concentrations of test substances were added on to the partial monolayer in microtiter plates. The plates were then incubated at 37° C. for 72 h in 5% $CO_2$ atmosphere, and microscopic examination was carried out and observations were noted every 24 h interval.

MTT ASSAY: After 72 h incubation, the drug solutions in the wells were discarded and 50 µl of MTT in PBS was added to each well. The plates were gently shaken and incubated for 3 h at 37° C. in 5% $CO_2$ atmosphere. The supernatant was removed and 100 µl of propanol was added and the plates were gently shaken to solubilize the formed formazan. The absorbance was measured using a microplate reader at a wavelength of 540 nm. The percentage growth inhibition was calculated using the standard formula and concentration of test substance needed to inhibit cell growth by 50% (CTC50) values was generated from the dose-response curves for each cell line.

Figure 4:
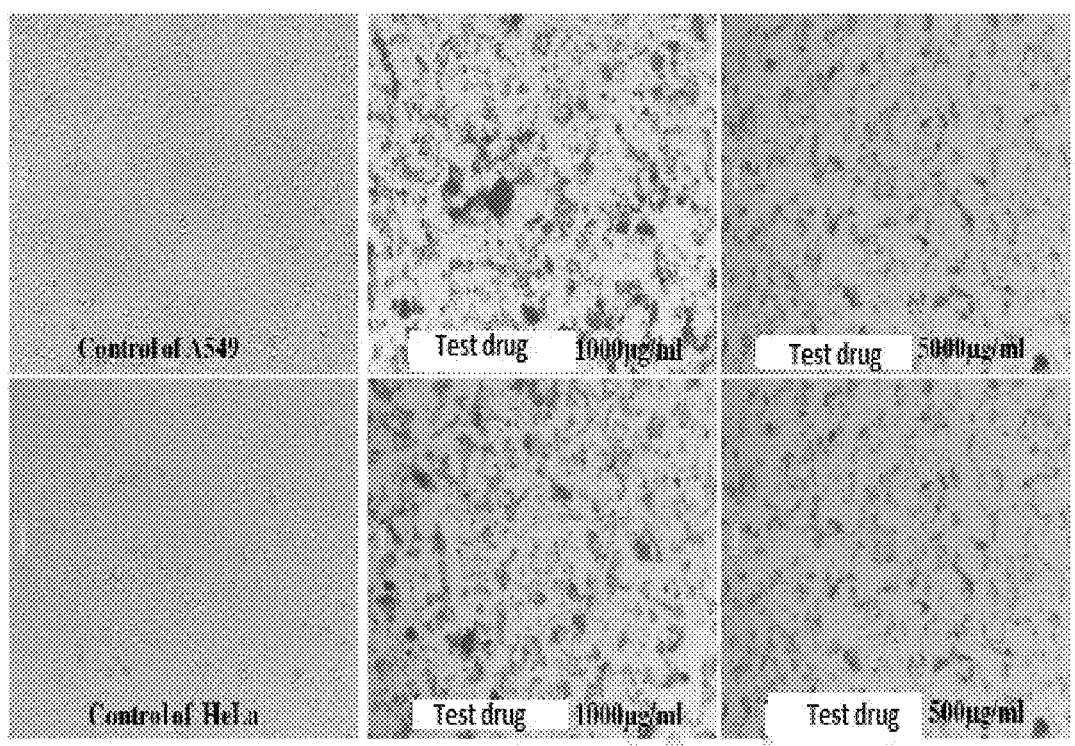
FIG. 4 illustrates the Cytotoxicity of test drug on A549 and HeLa cell lines.

Results:

FIG. 4 illustrates the Cytotoxicity of test drug on A549 and HeLa cell lines.

Table 7 depicts the Cytotoxic properties of test drug substance against A549 cell line.

TABLE 7

| Test Conc. (µg/ml) | % cytotoxicity | $CTC_{50}$ (µg/ml) |
|---|---|---|
| 1000 | 42.13 ± 0.17 | >1000 |
| 500 | 36.54 ± 0.26 | |
| 250 | 24.68 ± 0.43 | |
| 125 | 17.02 ± 0.75 | |
| 62.5 | 9.26 ± 0.35 | |
| 31.25 | 5.88 ± 0.28 | |
| 15.6 | 4.96 ± 0.28 | |
| 7.8 | 1.35 ± 0.35 | |

Table 8 depicts the cytotoxic properties of test drug substance against HeLa cell line

TABLE 8

| Test Conc. (µg/ml) | % cytotoxicity | $CTC_{50}$ (µg/ml) |
|---|---|---|
| 1000 | 48.99 ± 0.40 | >1000 |
| 500 | 40.87 ± 0.60 | |
| 250 | 35.28 ± 0.59 | |
| 125 | 31.62 ± 0.29 | |
| 62.5 | 28.27 ± 0.25 | |
| 31.25 | 23.35 ± 0.24 | |
| 15.6 | 12.38 ± 0.56 | |
| 7.8 | 6.80 ± 0.49 | |

Discussion and conclusion: Test drug Tablets were tested for in vitro cytotoxicity studies against A549 (Human Lung Carcinoma) and HeLa (Human Cervix Adenocarcinoma) cells by MTT assay exposing the cells to different concentrations of test substance. The test substances were taken at concentrations ranging from 1000 µg/ml to 7.8 g/ml to determine the percentage growth inhibition on the cell lines A549, and HeLa. The cell lines treated with the test drug exhibited a CTC50 value of >1000 (g/ml) on A549 and HeLa cell lines.

After 24 hours of administering the test drug, decrease in the nuclear area and increase in mitochondrial membrane potential and plasma membrane permeability were readily visible. Moreover the translocation of cytochrome C was also observed. The observation of the test sample indicated antiproliferative and apoptotic effects through up- and down regulation of apoptotic and anti-apoptotic proteins. The test sample showed significant effect on both intrinsic and extrinsic pathways. Moreover, the upregulation of p53 as well as the cell proliferation repressor proteins, p27 and p21, and the significant role of insulin/IGF-1 signaling were also identified. Moreover the caspases 3 and 8 were found to be significantly activated.

Example 6: In Vitro Anticancer Study of the Test Drug on Selected Cell Lines

Objective: The purpose of this Study is to evaluate the test substances for their cytotoxicity against selected cell lines.

Summary: In-vitro cytotoxicity of the test drug was tested through MTT assay on A549 (Human Lung Carcinoma), HeLa (Human Cervix Adenocarcinoma) and SKOV3 (Human Ovarian Cancer) cell lines. The test drug was administered at concentrations ranging from 1000 µg/ml to 7.8 g/ml to determine the percentage growth inhibition on the cell lines A549, HeLa and SKOV3. The test substances exhibited a $CTC_{50}$ value of >1000, >1000 and 403.67+1.84 respectively.

Method: The in vitro cytotoxicity was performed on A549 (Human Lung Carcinoma), HeLa (Human Cervix Adenocarcinoma), and SKOV3 (Human Ovarian Cancer) cell lines to find toxic concentration of the test drug by MTT assay.

Preparation of test solution: For cytotoxicity studies, 10 mg of all the eight test substances were separately dissolved and volume was made up with MEM/DMEM-HG supplemented with 2% inactivated FBS to obtain a stock solution of 1 mg/ml concentration and sterilized by 0.22µ syringe filtration. Serial two fold dilutions were prepared from this for carrying out cytotoxic studies.

Cell line and culture medium: A549 (Human Lung Carcinoma), HeLa (Human Cervix Adenocarcinoma) and SKOV3 (Human Ovarian Cancer) cell lines were procured from National Centre for Cell Sciences (NCCS), Pune, India. Stock cells were cultured in their respective media viz. MEM/DMEM HG/Ham's F-12 supplemented with 10% inactivated Fetal Bovine Serum (FBS), penicillin (100 IU/ml), streptomycin (100 µg/ml) and amphotericin B (5 µg/ml) in an humidified atmosphere of 5% $CO_2$ at 37° C. until confluent. The cells were dissociated with TPVG solution (0.2% trypsin, 0.02% EDTA, 0.05% glucose in PBS). The stock cultures were grown in 25 cc culture flasks and all experiments were carried out in 96 well microtiter plates (Tarsons India Pvt. Ltd., Kolkata, India).

Cytotoxicity studies: In all the cell lines, the monolayer cell culture was trypsinized and the cell count was adjusted to 100,000 cells/ml using respective media viz., MEM/DMEM-HG/Ham's F-12 containing 10% FBS. To each well of the 96 well microtiter plate, 0.1 ml of the diluted cell suspension was added. After 24 h, when a partial monolayer was formed, the supernatant was flicked off, monolayer washed once with medium and 100 µl of different test concentrations of test substances were added on to the partial monolayer in microtiter plates. The plates were then incubated at 37 degree C. for 72 hours in 5% $CO_2$ atmosphere, and microscopic examination was carried out and observations were noted every 24 hours interval.

MTT ASSAY: After 72 hours incubation, the drug solutions in the wells were discarded and 50 µl of MTT in PBS was added to each well. The plates were gently shaken and incubated for 3 hours at 37 degree C. in 5% CO2 atmosphere. The supernatant was removed and 100 µl of propanol was added and the plates were gently shaken to solubilize the formed formazan. The absorbance was measured using a microplate reader at a wavelength of 540 nm. The percentage growth inhibition was calculated using the standard formula and concentration of test substances needed to inhibit cell growth by 50% (CTC50) values was generated from the dose-response curves for each cell line.

Figure 5:
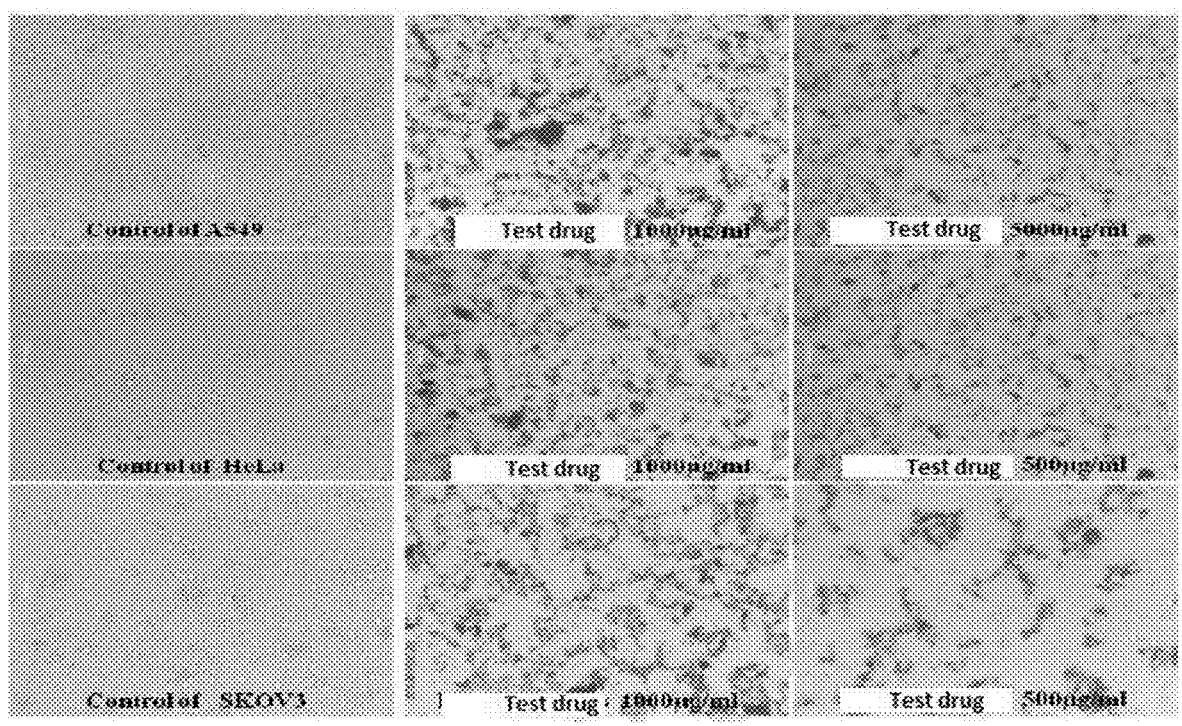
FIG. 5 illustrates the Cytotoxicity of test drug on A549, HeLa and SKOV3 cell lines.
Figure 6A:
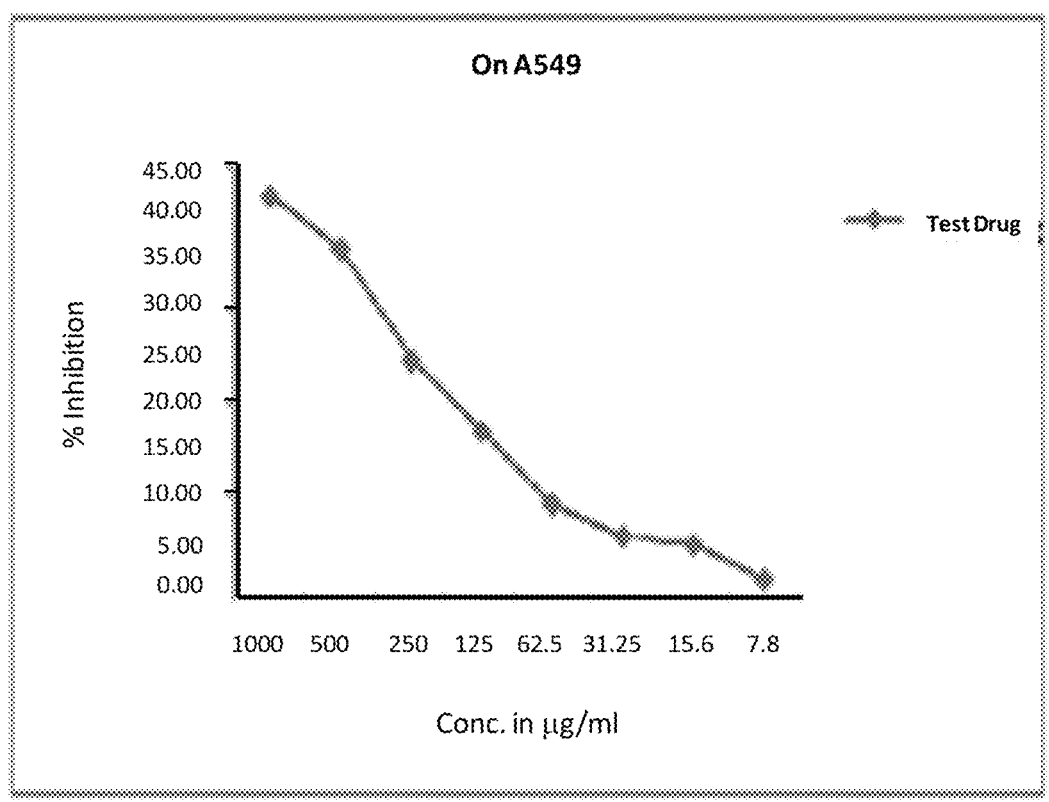
FIG. 6(*a*) is a graph depicting the cytotoxicity of test drug on A549 cell line.
Figure 6B:
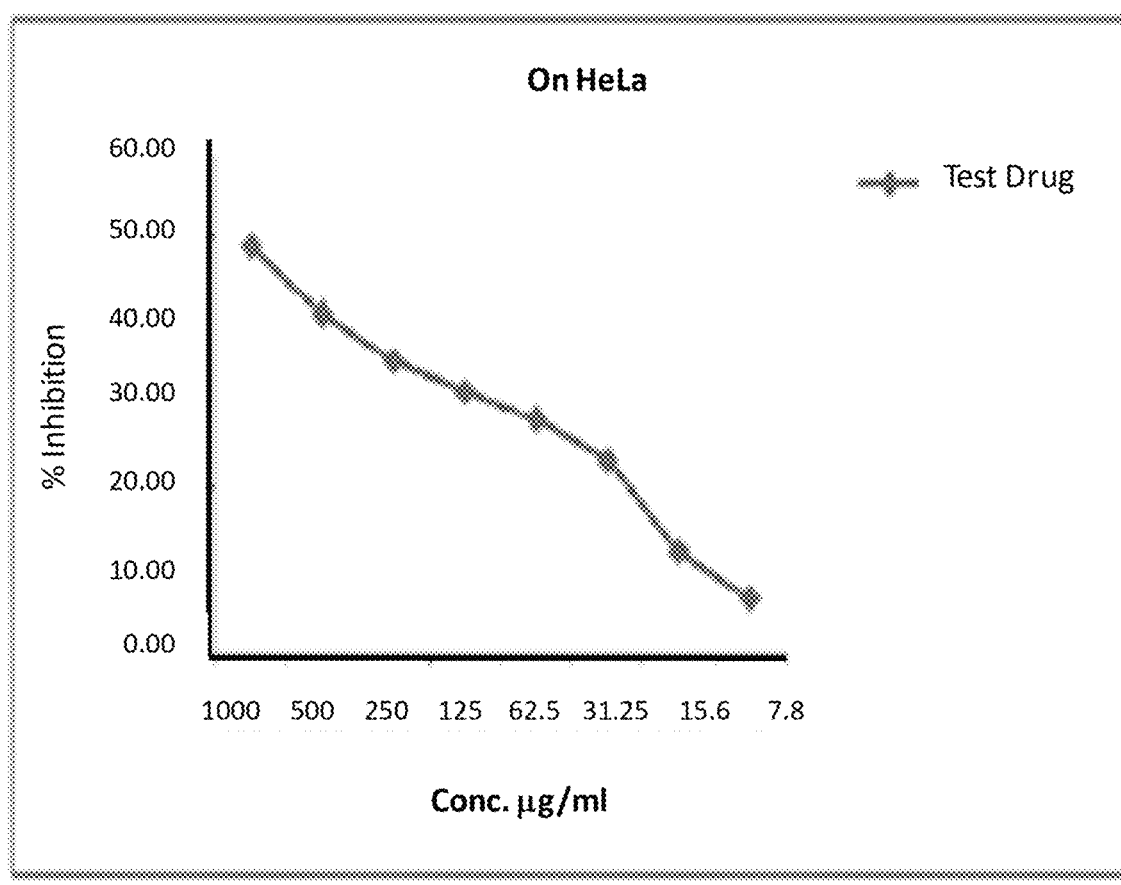
Figure 6C:
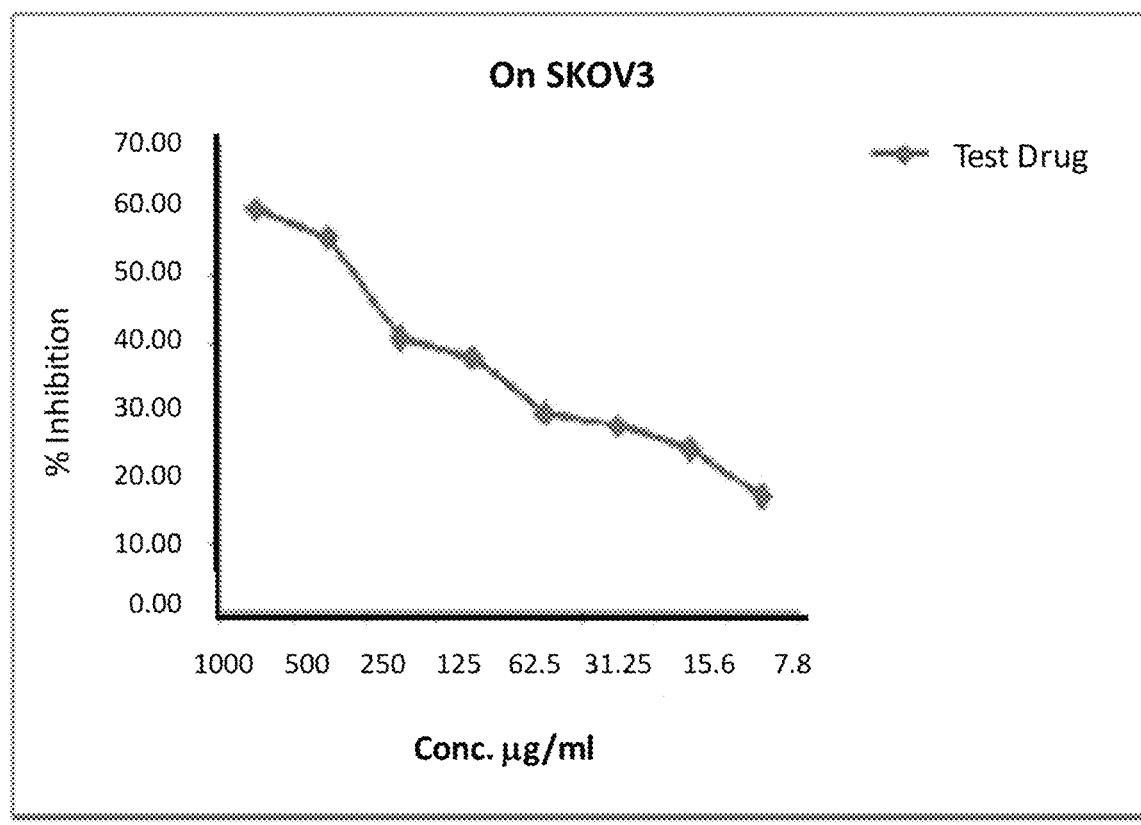

Results: FIG. 5 illustrates the Cytotoxicity of test drug on A549, HeLa and SKOV3 cell lines. FIG. 6(a) is a graph depicting the percentage growth inhibition of test drug on A549 cell line at different concentrations (1000 to 7.8 µg/ml). FIG. 6(b) is a graph depicting the percentage growth inhibition of test drug on HeLa cell line at different concentrations (1000 to 7.8 µg/ml). FIG. 6(c) is a graph depicting the percentage growth inhibition of test drug on SKOV3 cell line at different concentrations (1000 to 7.8 µg/ml). Table 9 depicts the Cytotoxic properties of test drug substance against A549 cell line.

TABLE 9

| Test Conc. (µg/ml) | % cytotoxicity | CTC$_{50}$ (µg/ml) |
|---|---|---|
| 1000 | 42.13 ± 0.17 | >1000 |
| 500 | 36.54 ± 0.26 | |
| 250 | 24.68 ± 0.43 | |
| 125 | 17.02 ± 0.75 | |
| 62.5 | 9.26 ± 0.35 | |
| 31.25 | 5.88 ± 0.28 | |
| 15.6 | 4.96 ± 0.28 | |
| 7.8 | 1.35 ± 0.35 | |

Table 10 depicts the Cytotoxic properties of test drug substance against HeLa cell line.

TABLE 10

| Test Conc. (µg/ml) | % cytotoxicity | CTC$_{50}$ (µg/ml) |
|---|---|---|
| 1000 | 48.99 ± 0.40 | >1000 |
| 500 | 40.87 ± 0.60 | |
| 250 | 35.28 ± 0.59 | |
| 125 | 31.62 ± 0.29 | |
| 62.5 | 28.27 ± 0.25 | |
| 31.25 | 23.35 ± 0.24 | |
| 15.6 | 12.38 ± 0.56 | |
| 7.8 | 6.80 ± 0.49 | |

Table 11 depicts the Cytotoxic properties of test drug substance against SKOV3 cell line.

TABLE 11

| Test Conc. (µg/ml) | % cytotoxicity | CTC$_{50}$ (µg/ml) |
|---|---|---|
| 1000 | 59.96 ± 0.38 | >403.67 ± 1.84 |
| 500 | 55.79 ± 0.18 | |
| 250 | 40.75 ± 0.42 | |
| 125 | 37.86 ± 0.43 | |
| 62.5 | 29.60 ± 0.25 | |
| 31.25 | 27.74 ± 0.48 | |
| 15.6 | 24.33 ± 1.01 | |
| 7.8 | 17.26 ± 0.3 | |

Discussion and conclusion: Test drug Tablets were tested for in vitro cytotoxicity studies against A549 (Human Lung Carcinoma) and HeLa (Human Cervix Adenocarcinoma) and SKOV3 (Human Ovarian Cancer) cells by MTT assay exposing the cells to different concentrations of test substance. The test substances were taken at concentrations ranging from ranging from 1000 µg/ml to 7.8 µg/ml to determine the percentage growth inhibition on the cell lines A549, HeLa and SKOV3. The test drug Tablets exhibited a CTC$_{50}$ value of >1000 (g/ml) on A549 and HeLa and and 403.671.84 g/ml on SKOV3 cell lines.

After 24 h treatment with treatment of test drug, decrease in the nuclear area and increase in mitochondrial membrane potential and plasma membrane permeability were readily visible. Moreover the translocation of cytochrome c also was observed. Test drug mediates its antiproliferative and apoptotic effects through up- and down regulation of apoptotic and antiapoptotic proteins. There was a significant involvement of both intrinsic and extrinsic pathways. Moreover, the upregulation of p53 as well as the cell proliferation repressor proteins, p27 and p21, and the significant role of insulin/IGF-1 signalling were also identified. Caspases3 and 8 were also found to be significantly activated.

Further, the following examples disclose details of clinical study performed with embodiments of the disclosed formulation. Embodiments of the formulations disclosed herein (also referred to as test drug) is described by reference to the following examples by way of illustration only, and should not be construed to limit the scope of the embodiments herein. It will be apparent to those skilled in the art that many modifications, both to materials and methods, may be practiced without departing from the scope of the claims.

Example 7

A patient having swelling in the anterior aspect of neck and no apparent constitutional symptoms was administered with the Test drug. The patient was suspected of having Papillary Carcinoma.

Cytological diagnosis revealed Hashimoto's thyroiditis with occasional papillary clusters. The swelling was firm, nodular and moving up during deglutition. No lymph nodes involved.

Blood Pressure: 150/100 mmHg.
Thyroid profile: T3: 112 ng/dL (normal range: 60-200)
T4: 2.6 µg/dL (normal range: 4.5-12.0)
TSH: 97.48 µIU/mL (normal range: 0.30-5.5)
It was observed that the swelling had markedly reduced in 45 days course of administration.
Blood Pressure: 140/86 mmHg.
Thyroid profile: T3: 101 ng/dL (normal range: 60-200)
T4: 6.3 µg/dL (normal range: 4.5-12.0)
TSH: 20.34 µIU/mL (normal range: 0.30-5.5)
The patient was administered with an embodiment of the disclosed formulation and observed for improvement. The TSH level improved and dropped to 5.2 µIU/mL with no clinical features.

Example 8

A patient having carcinoma of sigmoid colon, post-operative, post chemotherapy with the metastasis at Liver and Lungs and complaints of loss of appetite, gaseous distension of abdomen and mild cough was administered with the test drug at a dose of two 500 mg tablets twice daily. Patient was under constant observation. In due course, the patient exhibited substantial improvement in condition.

Table 12 depicts the results of the Liver function test (LFT). It was observed that the SGOT (Serum glutamic oxaloacetic transaminase) and SGPT (Serum glutamate pyruvate transaminase) levels which were elevated had significantly reduced with increase in appetite and reduction in gaseous distension of abdomen.

TABLE 12

| LFT data | | |
|---|---|---|
| Parameters | Before treatment | After treatment |
| Serum bilirubin: | | |
| Total | 0.83 mg/dl | 0.72 mg/dl |
| Direct | 0.3 mg/dl | 0.2 mg/dl |
| Indirect | 0.62 mg/dl | 0.52 mg/dl |
| Total protein | 6.6 mg/dl | 6.8 mg/dl |
| Albumin | 4.2 mg/dl | 4.4 mg/dl |
| Globulin | 2.4 mg/dl | 2.4 mg/dl |
| A:G Ratio | 1.75 mg/dl | 1.8 mg/dl |
| SGOT | 61.0 IU/L | 31.0 IU/L |
| SGPT | 74.0 IU/L | 24.0 IU/L |
| Alkaline Phosphatase | 201.0 IU/L | 96.0 IU/L |

Example 9

A diagnosed case of papillary carcinoma of thyroid, with a swelling in the anterior part of neck was administered with the Test drug. The patient was also a diagnosed case of Left Ventricular Hypertrophy and renal failure with complaints of general debility, loss of appetite, pedal edema and exertional dyspnea.

The test drug was administered periodically with regular follow up. Eventually, the patient showed improvement in all symptoms, and swelling of neck had reduced. Blood urea had reduced from 87.00 mg to 49.00 mg, serum creatinine improved from 2.1 to 1.8.

Thyroid Stimulating hormone reduced from 46.5 to 14.53 (normal: 0.3-5.5) which eventually got normalized (4.8 IU/ml).

In due course, this patient showed no symptoms of thyroid cancer and swelling in the neck was completely relieved.

Example 10

A patient with infiltrating ductal carcinoma of right breast, post-operative but without any chemotherapy or radiation was administered with the Test drug.

In due course, improvements in general condition like weight, appetite and hemoglobin was observed with no signs of metastasis. Table 13 depicts the changes in Hemoglobin level.

TABLE 13

Hemoglobin levels before and after treatment.

| Parameters | Before treatment | After treatment |
|---|---|---|
| Hemoglobin | 8.9 gm % | 12.7 gm % |

Example 11

A patient with bronchogenic carcinoma of the upper lobe of left lung having complaints of severe cough and breathlessness was administered with the Test drug for over a period. It was observed that the cough had reduced significantly with no signs of metastasis. Eventually, no serious episodes of symptoms were observed but with dramatic remission in respiratory symptoms. CT scan done indicated no signs of bronchogenic carcinoma.
Details:
The CT scan conducted before treatment showed pleural effusion and a lesion measuring about 4 cm in right upper lobe of lungs. After the treatment CT scan showed improvement. No cancer lesions were seen. Only emphysematous changes and fibrosis were noted.

Example 12

A patient with carcinoma of lung with severe adverse reactions of chemotherapy like weakness, vomiting, and oral ulcers was administered with the Test drug. The lesion was found to be chemo-resistant. Over a period, the symptoms like cough and breathlessness were considerably reduced; adverse effects of chemotherapy also subsided with no signs of metastasis.
Details:
Irregular lesion measuring about 4 cm in right middle lung near hilum, with mediastinal lymph node enlargement largest about 2 cm, pleural effusion on right side were observed.

Example 13

A diagnosed case of carcinoma of esophagus and hard palate having complaints of dysphagia, loss of appetite, loss of taste, general debility, and cough with whitish sputum was administered with the Test drug. In due course, the cough was substantially reduced, appetite improved and taste sensation was observed to be slightly better. USG of abdomen did not show any signs of metastasis. Follow up endoscopy indicated no signs of carcinoma.
Details:
Upper GI endoscopy done before treatment showed an ulceroproliferative growth in esophagus 11 cm from jaw level extending up to about 6.5 cm with narrowing lumen.

Endoscopy done post treatment showed no ulceroproliferative growth, mild fibrosis and slightly narrowed lumen was seen.

Example 14

A diagnosed case of bronchogenic carcinoma (post-operative and chemo resistant) having complaints of cough with hemoptysis, dyspnea and general debility was administered with the Test drug for over a period of time. The patient was also a known case of Type II Diabetes mellitus. In due course, it was observed that the complaints like hemoptysis, cough and dyspnea were drastically reduced.

Eventually, the patient was also observed to have become asymptomatic.
Details:
CT scan of lungs indicated no signs of carcinoma. Report of CT scan of lungs at the time of diagnosis showed a lesion of about 2.5×3 cm extending to hilum in right upper lobe of lungs with a few of hilar lymph nodes enlarged. Post treatment no lesions were observed, fibrous band with calcification was observed.

Example 15

A known case of adenocarcinoma of endometrium (post hysterectomy and post chemotherapy) with a history of recurrence as omental deposits was under the administration of the Test drug for a period of time. The patient was also a known case of diabetes mellitus type II and deep vein thrombosis having anemia, dyspnea on exertion, bilateral pedal edema, fullness and pain in abdomen. Abdomen USG were observed to be within normal limits, cancer markers CA-125 and CEA were also found to be with in normal limits. After continuous administration and observation over a period of time, symptoms like pedal edema and dyspnea had subsided, fullness and abdomen pain had been relieved.
Details:
Before treatment multiple peritoneal (omental deposits) with gross ascites were noted. After treatment no intraabdominal lesions were seen, no free fluid in abdomen and no organomegaly was observed. Over a period of time, CA-125 and CEA levels which initially were around 55.00 U/ml and 18.3 ng/mL, respectively, were reduced.

Example 16

A patient with h/o progressive swelling in right side of neck with pain, h/o weight loss, diagnosed to be the secondary of primary lesion at hypopharynx and suggested for neck dissection was under the administration of the Test drug. In due course, neck swelling had reduced, pain has subsided and general condition had stabilized. Also, serum LDH and CEA were observed to be within normal limits after treatment. Table 14 depicts the improvement in serum LDH and CEA levels before and after treatment.

TABLE 14

| Serum LDH and CEA | | |
| --- | --- | --- |
| Marker | Before treatment | After treatment |
| LDH | 1085 U/L | 296 U/L |
| CEA | 10.2 ng/mL | 1.5 ng/mL |

Example 17

A known case of adenocarcinoma of rectum post-operative and post chemo therapeutic status having h/o blood mixed stools, loss of appetite, progressive weight loss and general weakness was administered with the Test drug.

In due course, the patient has become asymptomatic with normal CA-125 and CEA levels. Follow up CT scan and USG reports were observed to be within normal limits after treatment.

Details:

Follow up CT scan report did not show any intra-abdominal lesion (However patient came after surgery, his first CT scan showed a lesion of about 3.5×4.5 cm in rectum with para coeliac lymph nodes enlarged)

USG report was normal without any intra-abdominal lesion, free fluid or organomegaly indicating no metastasis or new lesion Table 15 depicts the improvement in CA-125 and CEA levels before treatment (BT) and after treatment (AT). Weight improved by 4 kgs.

TABLE 15

| CA-125 and CEA levels | | |
| --- | --- | --- |
| Marker | BT | AT |
| CA-125 | 155.0 U/ml | 26.6 U/ml |
| CEA | 22.0 ng/ml | 3.3 ng/ml |

Example 18

A Non-Hodgkin's lymphoma patient, high grade large cell type with the h/o incomplete chemotherapy having symptoms of lymphadenopathy of left axillary and inguinal area, general debility and anemia was administered with the Test drug. The patient eventually has been observed to be asymptomatic.

Details:

CT scan taken before treatment showed multiple bilateral inguinal and cervical lymph node enlargement, and follow up CT scan showed no lymphadenopathy Follow up USG abdomen report shows no abnormality. No intraabdominal lymphadenopathy organomegaly or free fluid Biopsy report: Sections from the five lymph nodes received show normal architecture. The sections studied from the above lymph nodes do not show histological evidence of lymphoma. Table 16 depicts the LDH levels before and after treatment.

TABLE 16

| LDH report | | |
| --- | --- | --- |
| Parameters | Before treatment | After treatment |
| LDH | 630 U/L | 238 L |

Table 17 depicts the change in Hb % after treatment.

TABLE 17

| Hb % report | | |
| --- | --- | --- |
| Parameters | Before treatment | After treatment |
| Haemoglobin | 8.0 gm % | 13.8 gm % |

Table 18 depicts the results of LFT after treatment.

TABLE 18

| LFT report. |
| --- |

| Parameters | |
| --- | --- |
| Serum bilirubin: | |
| Total | 0.73 mg/dl |
| Direct | 0.3 mg/dl |
| Indirect | 0.42 mg/dl |
| Total protein | 7.1 mg/dl |
| Albumin | 4.6 mg/dl |
| Globulin | 2.5 mg/dl |
| A:G Ratio | 1.84 mg/dl |
| SGOT | 21.0 IU/L |
| SGPT | 14.0 IU/L |
| Alkaline Phosphatase | 98 IU/L |

Table 19 depicts the results of RFT after treatment.

TABLE 19

| RFT report. |
| --- |

| Parameters | |
| --- | --- |
| Serum creatinine | 1.1 mg/dl |
| Blood Urea | 38 mg/dl |
| Uric Acid | 5.4 mg/dl |

Example 19

A patient with the h/o colon cancer, post-operative having complaints of bloating of abdomen, urge to defecate after food and marginally elevated CEA levels, was administered with the Test drug for over a period.

Eventually, the patient was observed to become asymptomatic having CEA within normal limits. Table 20 depicts the CEA levels before and after treatment

TABLE 20

| CEA details before and after treatment. | | |
| --- | --- | --- |
| Parameters | Before treatment | After treatment |
| CEA | 102.0 ng/mL | 1.3 ng/mL |

Example 20

A diagnosed case of chronic myeloid leukemia having symptoms of pain in low back, thighs, intermittent fever and pain abdomen was administered with the Test drug for over a prolonged period. The patient was observed to become asymptomatic with WBC counts and morphology within normal limits.

Details:

Peripheral smear report showing WBC counts and morphology within normal limits are as follows: RBCs: Normocytic normochromic; WBCs: Within normal limits; Neutrophils: 62%; Lymphocytes: 32%; Monocytes: 01%; Basophils: 01%; Eosinophils: 04%.

Example 21

A diagnosed case of borderline mucinous tumor of right ovary hysterectomy was administered with the Test drug. Over a period, the general condition had improved. It was also observed that symptoms like abdominal distension and discomfort were completely relieved.

The patient was observed to become asymptomatic with normal levels of cancer markers and USG study.

Details:

USG report showed: Patient had a large tumor in right ovary (5.6×7.2 cm) with moderate ascites as was seen in her USG abdomen pelvis before treatment. Post-operative and after our treatment when USG was repeated no lesions, no free fluid, no organomegaly was observed, uterus was not visible as it was post hysterectomy status. Table 21 depicts the change in CA-125 and CA 19-9 levels.

TABLE 21

Cancer marker levels before and after treatment.

| Markers | Before treatment | After treatment |
|---|---|---|
| CA-125 | 65.00 U/ml | 14 U/ml |
| CA 19-9 | 68 U/ml | 18 U/ml |

Example 22

A known case of adenocarcinoma of colon with post-operative status, but without any chemotherapy had been administered with the Test drug for over a certain period.

Eventually, the patient was observed to become asymptomatic with no radiological, hematological or biochemical abnormalities.

Details:

X ray findings were as follows: No pleural effusion, no lesions, hilar lymph nodes normal, essentially a normal chest X ray was observed.

Hematological and biochemical results were as follows: Hb %: 14.2 gm %; RBCs: 5 million/cubic millimeter; WBCs: 7.8×109 L; Neutrophils: 64%; Lymphocytes: 32%; Monocytes: 0%; Basophils: 01%; Eosinophils: 03%.

Example 23

A diagnosed case of chronic lymphocytic leukemia having symptoms of intermittent fever, exhaustion, exertional dyspnea, multiple lymphadenopathy (especially axillary and cervical) was administered with the Test drug, without any allopathic intervention.

Eventually, it was observed that the lymphadenopathy had markedly reduced, fever relieved and LDH level had improved. Table 22 depicts the change in LDH levels after treatment.

TABLE 22

LDH levels before and after treatment.

| Parameter | Before treatment | After treatment |
|---|---|---|
| LDH | 656 U/L | 286 U/L |

The patient was observed to be comfortable except for a few episodes of dyspnea (the patient is a known case of bronchial asthma, diabetes mellitus and hypertension).

Example 24

A known case of recurrent fibro sarcoma, post-operative and incomplete chemotherapy status having swelling in right thigh, intermittent fever, and blood mixed stools and general debility was administered with the Test drug for over a period. Eventually, all symptoms were observed to have subsided except for edema in right lower limb. Further investigations showed no signs of recurrence.

Example 25

A known case of ovarian carcinoma with hepatic metastasis having features of tense ascites, general debility, and loss of appetite and pain in abdomen was administered with the Test drug. Over a period of time, ascites were observed to have been completely relieved, appetite improved and pain reduced. USG done after treatment showed no lesions in abdomen or pelvis, liver was normal and no free fluid in abdomen.

Details:

Follow up USG study of abdomen and CA-125 level were also observed to be normal. USG report before treatment showed a lesion measuring 3.2×4.6 cm in right ovary with multiple lesions in right lobe of liver, largest measuring 2.8 cm and gross ascites. Table 23 depicts the change in CA 125 levels after treatment.

TABLE 23

CA 125 levels before and after treatment.

| Markers | Before treatment | After treatment |
|---|---|---|
| CA-125 | 665.00 U/ml | 34 U/ml |

Example 26

A known case of adenocarcinoma of pancreas (unresectable) having complaints of distension and pain in abdomen was under the administration of the Test drug. Patient's follow up CT scan reports, during the course, indicated reduction in tumour mass. Patient was observed to have become asymptomatic.

Details:

CT scan report showed Moderate size (9.7×5.8×7.1 cm) lobulated hypoechoic soft tissue mass lesion in preaortic region. Over a period of time post treatment, the size of the lesion got reduced to 6.0×5.7 cm in head of pancreas with few areas of calcification.

Example 27

A diagnosed case of small cell carcinoma of cervix having complaints of watery and occasional blood tinged discharge per vagina and pain in lower abdomen was administered with the Test drug. In due course, the patient's PV examination was observed to be normal having healthy cervix without any discharge or touch bleed. Also, USG abdomen pelvis showed no abnormalities.

Details:

Per vaginal examination findings were as follows:
1. Labia minora, majora and clitoris: No lesions, scars, tears observed.
2. Inspection and palpation of vulva: The introitus—No discharge or bleeding, no ulcers, vaginal mucosa pinkish, no prolapse observed
3. Speculum examination: the labia are separated with the index finger and thumb of left hand. The lubricated closed speculum (correct size) is inserted through the introitus into the vaginal canal without any rotation i.e. closed blades are horizontal with speculum handles pointing posteriorly in the lithotomy position or anteriorly if using the examination couch. Cervix: Healthy with fibrosis (healed lesion), no touch bleed, slight serous discharge.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

I claim:

1. An oral formulation, comprising:
   *Withania somnifera* in an amount in the range of 6 to 10 wt. %;
   *Sida cordifolia* in an amount in the range of 6 to 10 wt. %;
   *Asparagus racemosus* in an amount in the range of 4 to 8 wt. %;
   *Tinospora cordifolia* in an amount in the range of 4 to 8 wt. %;
   *Moringa oleifera* in an amount in the range of 4 to 8 wt. %;
   *Picrorhiza kurroa* in an amount in the range of 4 to 8 wt. %;
   *Ocimum sanctum* in an amount in the range of 4 to 8 wt. %;
   *Curcuma longa* in an amount in the range of 5 to 9 wt. %;
   *Piper longum* in an amount in the range of 2 to 6 wt. %;
   *Piper nigrum* in an amount in the range of 2 to 6 wt. %;
   *Zingiber officinalis* in an amount in the range of 2 to 6 wt. %;
   *Terminalia chebula* in an amount in the range of 2 to 6 wt. %;
   *Terminalia bellerica* in an amount in the range of 2 to 6 wt. %;
   *Emblica officinalis* in an amount in the range of 2 to 6 wt. %;
   Shilajit in an amount in the range of 4 to 8 wt %;
   Abhraka Bhasma in an amount in the range of 2 to 4 wt. %;
   Trivanga Bhasma in an amount in the range of 0 to 2 wt %;
   Pravala Bhasma in an amount in the range of 0 to 2 wt. %;
   Loha Bhasma in an amount in the range of 2 to 4 wt. %; and
   Swarna Makshika Bhasma in an amount in the range of 0 to 2 wt. %, of the total formulation.

2. The formulation as claimed in claim 1, further comprising a suitable amount of gum *acacia*.

3. The formulation as claimed in claim 1, further comprising at least one additive selected from the group consisting of a flavor, a colorant, a preservative, and a pH adjuster.

4. The formulation as claimed in claim 1, wherein said formulation is in a form selected from the group consisting of powder, emulsion, tablets, capsules, troches and pills.

5. The formulation as claimed in claim 1, wherein said formulation is in the form of a tablet.

6. The formulation as claimed in claim 5, wherein said tablet is in the form of a 500 mg tablet.

7. A process for the preparation of formulation claimed in claim 1, comprising:
   levigating bhasmas and shilajit;
   adding finely powdered herbs; and
   adding grinding decoction while continuing grinding to obtain a ground mass.

8. The process for the preparation of a formulation as claimed in claim 7, wherein said finely powdered herbs comprises of finely powdered form of;
   *Withania somnifera* (Dried root), *Sida cordifolia* (Dried root), *Terminalia chebula* (Dry fruits), *Terminalia bellerica* (Dried fruits), *Emblica officinalis* (Dried fruits), *Asparagus racemosus* (Dried root), *Tinospora cordifolia* (Dried stem), *Piper longum* (Dried fruit), *Piper nigrum* (Dried fruit), *Zingiber officinalis* (Dried rhizome), *Moringa oleifera* (Dried stem bark), *Picrorhiza kurroa* (Dried root), *Ocimum sanctum* (Dried leaves) and *Curcuma longa* (Dried rhizome).

9. The process for the preparation of a formulation as claimed in claim 7, wherein said grinding decoction is a decoction of at least one herb selected from the group consisting of *Aegle marmelos, Premna mucronata, Oroxylum indicum, Steriospermum suaveolens, Gmelina arborea, Solanum indicum, Solanum xanthocarpum, Tribulus terrestris, Uraria picta, Desmodium gangeticum, Vica rosea, Semecarpus anacardium, Asparagus racemosus, Momordica charantia, Acacia catechu, Ocimum sanctum, Rubia cordifolia, Bauhinia variegate, Adhatoda vasica, Eclipta alba, Moringa oleifera, Cynodon dactylon, Tinospora cordifolia, Crotolaria juncea, Cuminum cyminum, Smilax china, Mimosa pudica, Calotropis procera, Sida rombifolia, Murraya koeinigi* and *Trichosanthus dioica*.

10. A method of inducing a cytotoxic, apoptotic, antiproliferative, and/or growth inhibitory effect in cancer cells comprising:
    treating said cancer cells with a formulation claimed in claim 1.

11. A method of treating cancer comprising administering a therapeutically effective amount of the formulation claimed in claim 1.

12. The method of treating cancer as claimed in claim 11, wherein said effective amount of the formulation is 1000 mg tablets thrice a day.

13. The method as claimed in claim 11, wherein said formulation is administered along with administration of at least one other cancer medication.

14. The method as claimed in claim 13 wherein said at least one other cancer medication is selected from chemotherapy and radiotherapy.

15. The formulation as claimed in claim 2, wherein said *Withania somnifera* is in an amount of 8 wt. %; *Sida cordifolia* is in an amount of 8 wt. %; *Asparagus racemosus* is in an amount of 6 wt. %; *Tinospora cordifolia* is in an amount of 6 wt. %; *Moringa oleifera* is in an amount of 6 wt. %; *Picrorhiza kurroa* is in an amount of 6 wt. %; *Ocimum sanctum* is in an amount of 6 wt. %; *Curcuma longa* is in an amount of 7 wt. %; *Piper longum* is in an amount of 4 wt. %; *Piper nigrum* is in an amount of 4 wt. %; *Zingiber officinalis* is in an amount of 4 wt. %; *Terminalia chebula* is in an amount of 4 wt. %; *Terminalia bellerica* is in an amount of 4 wt. %, *Emblica officinalis* is in an amount of 4 wt. %; Shilajit is in an amount of 6 wt %; Abhraka Bhasma is in an amount of 2 wt. %; Trivanga Bhasma is in an amount of 1 wt %; Pravala Bhasma is in an amount of 1 wt. %; Loha Bhasma is in an amount of 2 wt. %; Swarna Makshika Bhasma is in an amount of 1 wt. %; and Gum *acacia* is in an amount of 10 wt. %, of the total formulation.

\* \* \* \* \*